United States Patent
Kolenbrander et al.

(10) Patent No.: US 7,556,611 B2
(45) Date of Patent: Jul. 7, 2009

(54) EXTRACORPOREAL BLOOD PROCESSING APPARATUS WITH PUMP BALANCING

(75) Inventors: Jeremy Kolenbrander, Brighton, CO (US); William Palsulich, Lakewood, CO (US); James Ladtkow, Broomfield, CO (US); Dave Tyler, Lakewood, CO (US); Jeffrey A. Steward, Lakewood, CO (US); Dave Gibbons, Highlands Ranch, CO (US); John R. Lindner, Morrison, CO (US)

(73) Assignee: CaridianBCT, Inc., Lakewood, CO (US)

( * ) Notice: Subject to any disclaimer, the term of this patent is extended or adjusted under 35 U.S.C. 154(b) by 0 days.

(21) Appl. No.: 11/563,898

(22) Filed: Nov. 28, 2006

(65) Prior Publication Data
US 2007/0243990 A1 Oct. 18, 2007

Related U.S. Application Data

(60) Provisional application No. 60/745,051, filed on Apr. 18, 2006.

(51) Int. Cl.
*A61M 37/00* (2006.01)
*G05D 9/00* (2006.01)
*G01F 1/12* (2006.01)

(52) U.S. Cl. .............. 604/6.11; 604/4.01; 604/6.01; 700/281; 702/100

(58) Field of Classification Search ............ 37/318, 37/319, 322, 323; 175/67, 312, 339, 340, 175/393, 424; 166/66.5; 299/17; 604/6.1, 604/6.01, 6.11; 700/281; 702/100
See application file for complete search history.

(56) References Cited

U.S. PATENT DOCUMENTS

| 3,375,886 A | 4/1968 | Goodwin et al. ............. 175/66 |
| 3,416,614 A | 12/1968 | Goodwin et al. ............. 175/67 |
| 3,489,280 A | 1/1970 | Israelson et al. ............ 209/223 |
| 3,831,753 A | 8/1974 | Gaylord et al. ............. 209/399 |
| 3,952,857 A | 4/1976 | Nazuka ....................... 198/41 |

(Continued)

FOREIGN PATENT DOCUMENTS

DE 2052516 4/1972

(Continued)

OTHER PUBLICATIONS

International Search Report dated Sep. 13, 2004 (PCT/EP2004/051407).

(Continued)

*Primary Examiner*—Tatyana Zalukaeva
*Assistant Examiner*—Susan Su
(74) *Attorney, Agent, or Firm*—John R. Merkling; Edna M. O'Connor; Laura Butterfield Arciniegas

(57) ABSTRACT

An extracorporeal blood processing system having a centrifugal rotor, a control system, a plurality of peristaltic pumps, and a removable tubing circuit wherein blood components can be processed. A pump-balancing process, implemented by the control system, causes selected pumps to fill and empty a reservoir in the tubing circuit. Ratios of displaced volume per pump revolution or other pumping action can be used by the control system to increase the effectiveness and efficiency of the donation process. The pump-balancing process may be performed during priming or set-up of the blood processing system or during an actual donation.

26 Claims, 18 Drawing Sheets

U.S. PATENT DOCUMENTS

| | | | |
|---|---|---|---|
| 4,137,913 A | | 2/1979 | Georgi |
| 4,275,726 A | * | 6/1981 | Schael ........................ 604/6.06 |
| 4,322,972 A | * | 4/1982 | Karjala ........................ 73/168 |
| 4,486,189 A | | 12/1984 | Troutner et al. |
| 4,655,742 A | | 4/1987 | Vantard |
| 4,769,001 A | * | 9/1988 | Prince ........................ 604/6.07 |
| 4,897,797 A | * | 1/1990 | Free et al. .................... 700/266 |
| 4,923,439 A | | 5/1990 | Seidel et al. |
| 4,954,128 A | * | 9/1990 | Ford ........................... 604/6.05 |
| 4,993,503 A | | 2/1991 | Fischer et al. ................. 175/62 |
| 5,170,891 A | | 12/1992 | Barrett ..................... 209/223.2 |
| 5,470,483 A | * | 11/1995 | Bene et al. ................... 210/741 |
| 5,522,998 A | | 6/1996 | Polaschegg |
| 5,702,358 A | * | 12/1997 | Witherspoon et al. ........ 604/6.1 |
| 5,941,842 A | | 8/1999 | Steele et al. |
| RE36,386 E | * | 11/1999 | Abbott et al. .............. 604/6.13 |
| 6,071,258 A | | 6/2000 | Dalke et al. |
| 6,083,187 A | * | 7/2000 | Nakayama et al. ......... 604/6.01 |
| 6,139,748 A | * | 10/2000 | Ericson et al. .............. 210/646 |
| 6,412,643 B1 | | 7/2002 | Wysolmierski ............. 209/213 |
| 6,497,674 B1 | | 12/2002 | Steele et al. |
| 6,510,907 B1 | | 1/2003 | Blange ........................ 175/67 |
| 6,702,940 B2 | | 3/2004 | Blange ........................ 210/222 |
| 6,759,007 B1 | * | 7/2004 | Westberg et al. .............. 422/44 |
| 6,790,195 B2 | | 9/2004 | Steele et al. |
| 6,899,691 B2 | * | 5/2005 | Bainbridge et al. ......... 604/4.01 |
| 2002/0079998 A1 | * | 6/2002 | Blange ........................ 335/302 |
| 2002/0147423 A1 | * | 10/2002 | Burbank et al. ............ 604/6.16 |
| 2004/0236263 A1 | | 11/2004 | Van Waeg et al. |
| 2005/0000868 A1 | | 1/2005 | Weigel et al. |
| 2006/0000759 A1 | * | 1/2006 | Takao et al. ............... 210/198.2 |
| 2006/0124548 A1 | * | 6/2006 | Okazaki ..................... 210/646 |
| 2006/0185907 A1 | | 8/2006 | Blange ........................ 175/424 |

FOREIGN PATENT DOCUMENTS

| | | |
|---|---|---|
| DE | 2832037 | 1/1980 |
| GB | 924334 | 4/1982 |
| WO | 02/34653 | 5/2002 |
| WO | 02/092956 | 11/2002 |
| WO | WO2005005767 | 1/2005 |
| WO | WO2005005768 | 1/2005 |
| WO | WO2005038189 | 4/2005 |
| WO | WO2005040546 | 5/2005 |

OTHER PUBLICATIONS

International Search Report for corresponding application PCT/US06/45502 with Written Opinion, mailed Oct. 29, 2007.

* cited by examiner

EXTRACORPOREAL BLOOD PROCESSING APPARATUS WITH PUMP BALANCING

FIELD OF THE INVENTION

The present invention generally relates to the field of extracorporeal blood processing and, more particularly, to methods and apparatus which may be incorporated into an apheresis system.

BACKGROUND OF THE INVENTION

One type of extracorporeal blood processing is an apheresis procedure in which blood is removed from a donor or patient, directed to a blood component separation device such as a centrifuge, and separated into red blood cells, white blood cells, platelets, plasma or other blood components for collection or therapeutic purposes. One or more of these blood component types are collected, while the remainder is returned to the donor or patient.

An apheresis system includes a blood component separation device, such as a membrane-based separation device or a centrifuge, which separates blood into red blood cells, white blood cells, platelets, or plasma. In one embodiment, the separation device includes a rotor containing a channel that receives a blood-processing vessel. Typically, an extracorporeal tubing circuit connects a healthy human donor or a patient suffering from some type of illness with the blood-processing vessel. The blood processing vessel and extracorporeal tubing circuit collectively define a sterile system. When the fluid connection is established, blood may be extracted from the donor/patient (hereafter, "donor") and directed to the blood component separation device such that at least one type of blood component may be separated and removed from the blood, either for collection or for therapy. Peristaltic pumps on the separation device act on segments of the tubing circuit to extract blood from the donor, direct it to the appropriate processing location, add appropriate amounts of anti-coagulant, store separated blood components, and, finally, return residual blood components to the donor. It is advantageous that the relative action of the pumps be known, so that the appropriate amounts of fluid can be used in the blood separation process. Since a new tubing circuit is uniquely installed in the device for each donation, and since there may be variation between tubing circuits and in the exact interconnection between the tubing circuit and the separation device, it would be advantageous if the action of the pumps could be tested in connection with each donation.

SUMMARY OF THE INVENTION

The present invention generally relates to extracorporeal blood processing. Since each of the various aspects of the present invention may be incorporated into an apheresis system, the present invention will be described in relation to this particular application. However, at least certain of the aspects of the present invention may be suited for other extracorporeal blood processing applications and such are within the scope of the present invention.

An extracorporeal blood processing system comprises a blood separation device having a centrifugal rotor, a control system, a plurality of peristaltic pumps, and a removable tubing circuit wherein blood and blood components can be collected and processed. A pump-balancing process, implemented by the control system, causes selected pumps to fill and empty a reservoir in the tubing circuit. Ratios of displaced volume per pump revolution or other pimping action can be obtained. These ratios may be used by the control system in connection with an operating protocol to increase the effectiveness and efficiency of the donation process. The pump-balancing process may be performed during priming or set-up of the blood processing system or during an actual donation. The pump-balancing process may also be performed more than once during a donation.

DETAILED DESCRIPTION

The present invention will be described in relation to the accompanying drawings, which assist in illustrating the pertinent features thereof.

Figure 1:
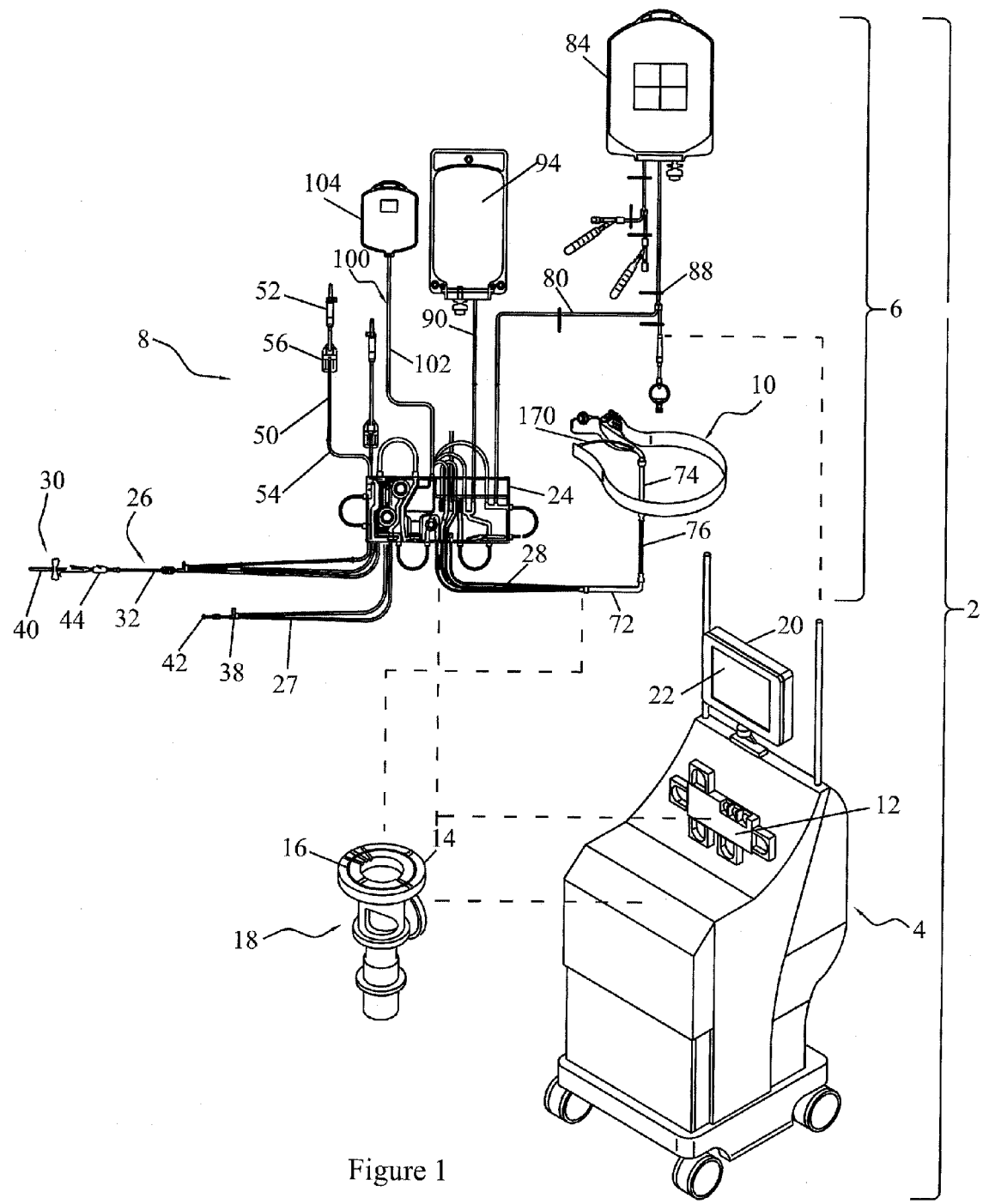
FIG. 1 is a perspective view of one embodiment of an apheresis system with an extracorporeal tubing circuit and cassette assembly.

A blood apheresis system 2, as illustrated in FIG. 1, allows for a continuous blood component separation process. Whole blood is withdrawn from a donor and is provided to a blood component separation device 4 where the blood is separated into the various component types and at least one of these blood component types is collected. These blood components may then be provided for therapeutic purposes.

In the blood apheresis system 2, blood is withdrawn from the donor and directed through a disposable set 6, which includes an extracorporeal tubing circuit 8 and a blood processing vessel 10 and which defines a sterile system. The disposable set 6 is mounted on the blood component separation device 4, as shown by a dotted line in FIG. 1. A pump/valve/sensor assembly 12 interfaces with a cassette 24 in the extracorporeal tubing circuit 8. A channel assembly 14, mounted within the separation device 4 but illustrated separately in FIG. 1, is connected with a rotatable centrifuge rotor assembly 18, which provides the centrifugal forces required to separate blood into various blood components. The blood-processing vessel 10 fits into a channel housing 16 in the channel assembly 14. Blood thus flows from the donor, through the extracorporeal tubing circuit 8, and into the rotating blood processing vessel 10. The blood within the blood-processing vessel 10 is separated into various blood components and at least one of these blood components (e.g., platelets, plasma, red blood cells) is continually removed from the blood-processing vessel 10. Blood components that are not being retained for collection or for therapeutic treatment are also removed from the blood-processing vessel 10 and returned to the donor via the extracorporeal tubing circuit 8.

One or more microprocessors form a control system, which controls operation of the blood component separation device 4. Microcomputers may also accommodate interfaces with devices such as CD ROM, modem, audio, networking and other capabilities. In order to assist the operator of the apheresis system 2 with various aspects of its operation, the blood component separation device 4 includes a graphical interface 20 with a touch screen 22.

Figure 2:
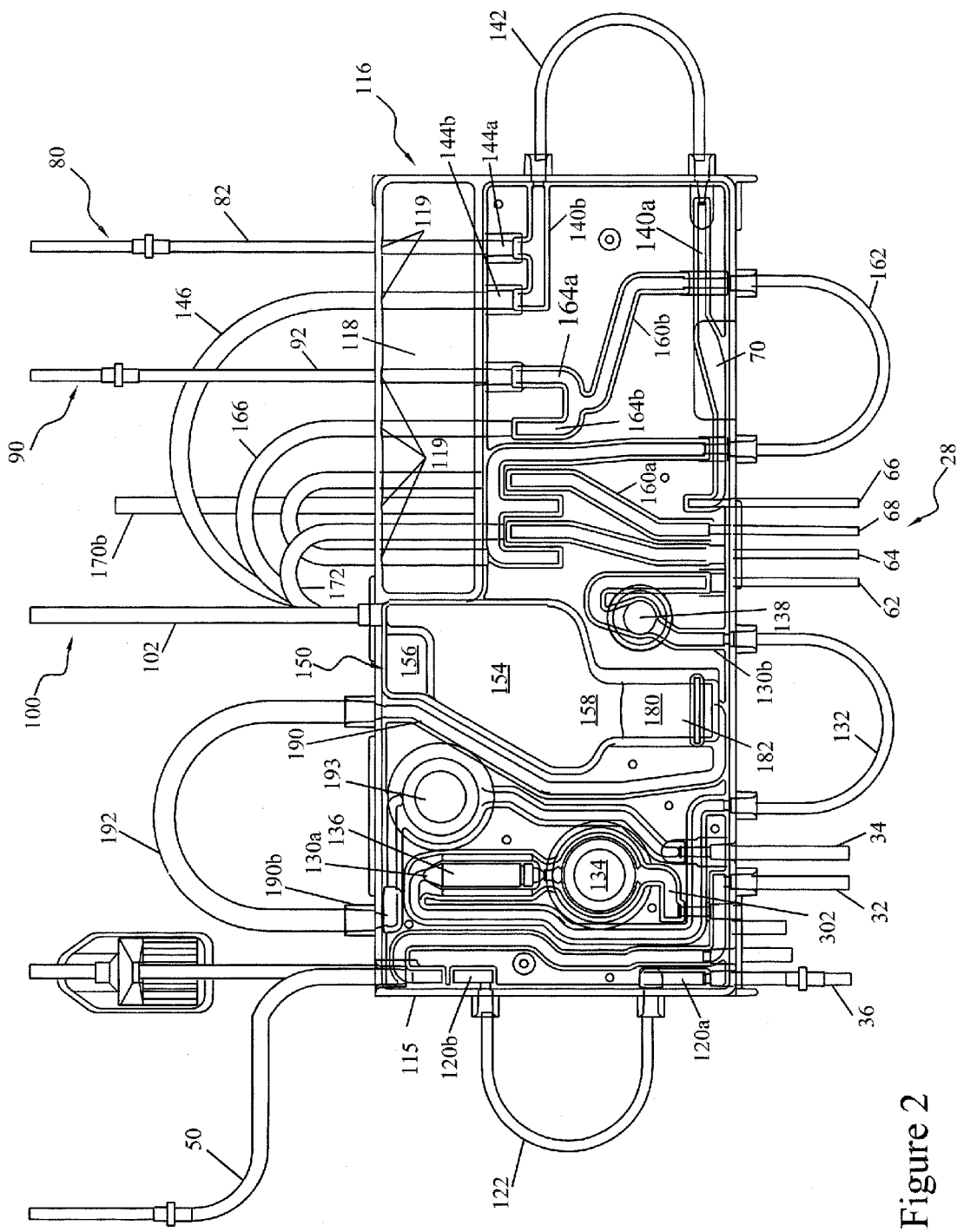
FIG. 2 illustrates the cassette assembly for the system of FIG. 1.

As illustrated in FIGS. 1 and 2, extracorporeal tubing circuit 8 forms a blood processing path for conducting blood through the blood apheresis system 2. The tubing circuit 8 comprises a cassette assembly 24 and a number of tubing assemblies. Generally, blood removal tubing assembly 26 and blood return tubing assembly 27 provide a dual-needle interface between a donor and cassette assembly 24, and blood inlet/blood component tubing subassembly 28 provides the interface between cassette assembly 24 and blood processing vessel 10. An anticoagulant tubing assembly 50, platelet collection tubing assembly 80, plasma collection tubing assembly 90, and vent bag tubing subassembly 100 are also connected with cassette assembly 24. The extracorporeal tubing circuit 8 and blood-processing vessel 10 are connected to yield a sterile disposable for a single use.

The blood removal tubing assembly 26 includes a needle subassembly 30 connected with blood removal tubing 32 and anticoagulant tubing 36 (see FIG. 2). The blood return tubing assembly 27 includes blood return tubing 34 connected with a second needle subassembly 38. The blood removal needle subassembly 30 includes a needle 40 having a protective needle sleeve and needle cap (not shown). Needle subassembly 30 may include a sleeve and tubing clamp 44 positioned about the tubing 32. The blood return needle subassembly 38 also includes a needle 42 having a protective needle sleeve and needle cap (not shown). As known in the art, a single needle assembly could also be used both to withdraw blood and return blood components to the patient or donor.

Cassette assembly 24 includes front and back molded plastic plates 112 and 114 (see FIG. 4) that are welded together to define a rectangular cassette member 15 having integral fluid passageways. The cassette assembly 24 further includes a number of outwardly extending tubing loops connecting various integral passageways. The integral passageways are also connected to the various tubing assemblies.

Cassette assembly 24 includes a first integral anticoagulant passageway 120a connected with the anticoagulant tubing 36 of the blood removal/return tubing assembly 26. The cassette assembly 24 further includes a second integral anticoagulant passageway 120b and a pump-engaging, anticoagulant tubing loop 122 between the first and second integral anticoagulant passageways 120a, 120b. The second integral anticoagulant passageway 120b is connected with anticoagulant tubing assembly 50. The anticoagulant tubing assembly 50 includes a spike drip chamber 52 connectable to an anticoagulant source, anticoagulant feed tubing 54, and a sterile barrier filter 56. During use, the anticoagulant tubing assembly 50 supplies anticoagulant to the blood removed from a donor to reduce or prevent any clotting in the extracorporeal tubing circuit 8.

Cassette assembly 24 also includes a first integral blood inlet passageway 130a connected with blood removal tubing 32 of the blood removal/return tubing assembly 26. The cassette assembly 24 further includes a second integral blood inlet passageway 130b and a pump-engaging, blood inlet tubing loop 132 between the first and second integral blood inlet passageways 130a, 130b. The first integral blood inlet passageway 130a includes a first pressure-sensing module 134 and inlet filter 136, and the second integral blood inlet passageway 130b includes a second pressure-sensing module 138. The second integral blood inlet passageway 130b is connected with blood inlet tubing 62 of the blood inlet/blood component tubing assembly 28.

Blood inlet tubing 62 is also connected with input port 170 of blood processing vessel 10 to provide whole blood thereto for processing. To return separated blood components to cassette assembly 24, the blood inlet,blood component tubing assembly 28 further includes red blood cell (RBC) outlet tubing 64, platelet outlet tubing 66 and plasma outlet tubing 68 connected with corresponding outlet ports of blood processing vessel 10. The blood inlet tubing 62, RBC outlet tubing 64, plasma outlet tubing 68 and platelet outlet tubing 66 all pass through first and second strain relief members 72 and 74 and a braided bearing member 76 therebetween. This advantageously allows for a sealless connection, as taught in U.S. Pat. No. 4,425,112. Multi-lumen connectors can be employed in the various tubing lines.

Platelet outlet tubing 66 of the blood input/blood component tubing assembly 28 includes a transparent integral cuvette 70 for detecting red blood cells via an interfacing RBC spillover detector provided on blood component separation device 4. Platelet outlet tubing 66 connects with a first integral platelet passageway 140a of cassette assembly 24.

The cassette assembly 24 further includes a pump-engaging, platelet-tubing loop 142 connecting the first integral platelet passageway 140a and a second integral platelet passageway 140b. The second integral platelet passageway 140b includes first and second spurs 144a and 144b, respectively. The first spur 144a is connected with platelet collection tubing assembly 80.

The platelet collection tubing assembly 80 can receive separated platelets during operation and includes platelet collector tubing 82 and platelet collection bag 84 connected thereto. Slide clamps 88 are provided on platelet collector tubing 82.

The second spur 144b of the second integral platelet passageway 140b is connected with platelet return tubing loop 146 of the cassette assembly 24 to return separated platelets to a donor, for example, upon detection of RBC spillover during platelet collection. For such purpose, platelet return tubing loop 146 is connected to the top of a blood return reservoir 150 integrally formed by the molded front and back plates 112, 114 of cassette member 115. As will be further described, one or more types of uncollected blood components, collectively referred to as return blood, will cyclically accumulate in and be removed from reservoir 150 during use. Back plate 114 of the cassette member 115 also includes an integral frame corner 116 defining a window 118 through a corner of cassette member 115. The frame corner 116 includes keyhole recesses 119 for receiving and orienting the platelet collector tubing 82 and platelet return tubing loop 146 in a predetermined spaced relationship within window 118.

The plasma outlet tubing 68 of blood inlet/blood component tubing assembly 28 connects with a first integral plasma passageway 160a of cassette assembly 24. Cassette assembly 24 includes a pump-engaging, plasma-tubing loop 162 connecting the first integral plasma passageway 160a and a second integral plasma passageway 160b. The second integral plasma passageway 160b includes first and second spurs 164a and 164b. The first spur 164a connects to the plasma collection tubing assembly 90.

The plasma collection tubing assembly 90 includes plasma collector tubing 92 and plasma collection bag 94. A slide clamp may be provided on plasma collector tubing 92.

The second spur 164b of the second integral plasma passageway 160b connects to a plasma return tubing loop 166 to return plasma to donor. For such purpose, the plasma return tubing loop 166 connects to the top of the blood return reservoir 150 of the cassette assembly 24. Again, keyhole recesses 119 in the frame 116 of cassette assembly 24 maintain the plasma collector tubing 92 and plasma return tubing loop 166 in a predetermined spaced relationship within window 118.

The RBC outlet tubing 64 of the blood inlet/blood component tubing assembly 28 connects with integral RBC passageway 170 of cassette assembly 24. The integral RBC passageway 170 includes first and second spurs 170a and 170b, respectively. The first spur 170a connects with RBC return tubing loop 172 to return separated RBC to a donor. The RBC return tubing loop 172 connects to the top of blood return reservoir 150 of the cassette assembly 24. The second spur 170b may be closed off as shown, or may be connected with an RBC collection tubing assembly (not shown) for collecting RBC. Keyhole recesses 119 of the frame 116 maintain the RBC return tubing loop 172 in a desired orientation within window 118.

Vent bag tubing assembly 100 is also connected to the top of blood return reservoir 150 of cassette assembly 24. The vent bag tubing assembly 100 includes vent tubing 102 and a vent bag 104. During use, sterile air present since packaging within cassette assembly 24, and particularly within blood return reservoir 150, cyclically passes into and back out of vent tubing 102 and vent bag 104.

Vent bag 104 may be provided with a sterile, gas pressure-relief valve (not shown) at a top end. Instead of vent bag tubing assembly 100, additional integral passageways, integrated chambers and tubing loops could be included in cassette assembly 24 to perform the same functions as the vent bag tubing assembly 100.

The platelet return tubing loop 146, plasma return tubing loop 166 and RBC return tubing loop 172 are connected in a row to the top of blood return reservoir 150 immediately adjacent to forwardly projecting sidewalls 152 thereof so that the blood components returned thereby will flow down the inner walls of the blood return reservoir 150. The blood return reservoir 150 includes an enlarged, forwardly projecting midsection 154, a reduced top section 156 and reduced bottom section 158 (see also FIG. 4). A filter 180 is disposed in a bottom cylindrical outlet 182 of the blood return reservoir 150.

A first integral blood return passageway 190a is connected to the outlet 182 of blood return reservoir 150, and is further connected to a second integral blood-return passageway 190b via a pump-engaging, blood return tubing loop 192. The second integral blood-return passageway 190b comprises a third pressure-sensing module 193 and is connected with the blood return tubing 34 of the blood return tubing assembly 26 to return blood to the donor via blood return needle 42.

As illustrated in FIG. 2, pump-engaging tubing loops 122, 132, 142, 162 and 192 extend from cassette member 115 to yield an asymmetric arrangement thereby facilitating proper mounting of cassette assembly 24 on blood component separation device 4 for use. To further facilitate loading of cassette assembly 24, it is noted that the back plate 114 of cassette member 115 is preferably molded to present a shallow pan-shaped back having a rim extending around the entire periphery and around window 118, the edge of the rim being substantially coplanar with the back surface of the top, mid and bottom sections 154, 156, 158 of reservoir 150 and further defining a recessed region within which first, second, and third pressure sensing modules 134,138, and 193 project.

Figure 3:
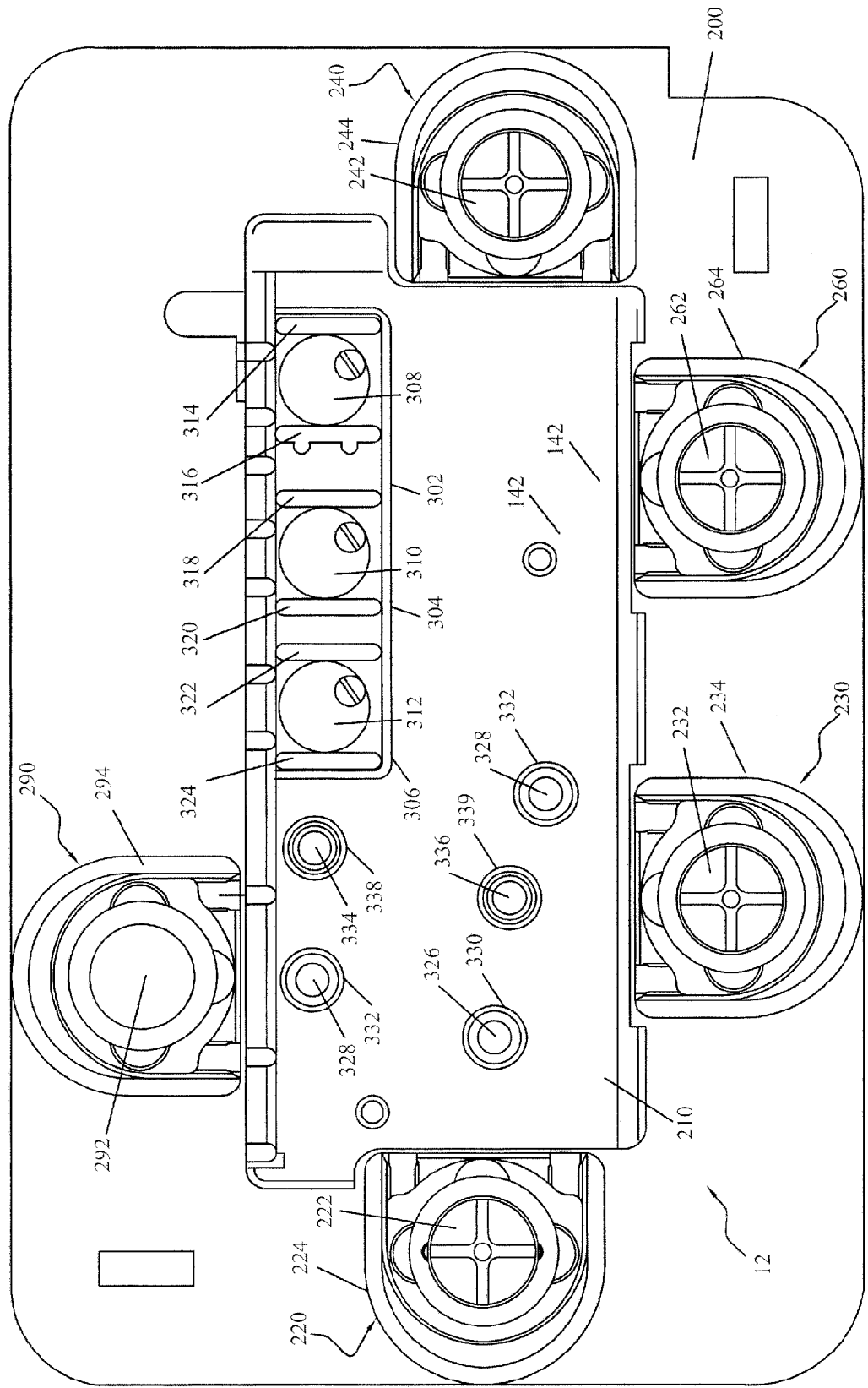
FIG. 3 is a front view of a pump/valve/sensor assembly for the system of FIG. 1.

Cassette assembly 24 is mounted upon and operatively interfaces with the pump/valve/sensor assembly 12 of blood component separation device 4 during use. The pump/valve/sensor assembly 12 is angled upward at about 45°. As illustrated in FIG. 3 the pump/valve/sensor assembly 12 includes a cassette mounting plate 210, and a number of peristaltic pump assemblies, flow-divert valve assemblies, pressure sensors and ultrasonic level sensors connected to face plate 200 of blood collection device 4 for pumping, controlling and monitoring the flow of blood components through extracorporeal tubing circuit 8 during use. Anticoagulant pump assembly 220 receives anticoagulant tubing loop 122; blood inlet pump assembly 230 receives blood inlet tubing loop 132; platelet pump assembly 240 receives platelet tubing loop 142; plasma pump assembly 260 receives plasma tubing loop 162; and blood return pump assembly 290 receives blood return tubing loop 192. Each of the peristaltic pump assemblies 220, 230, 240, 260, and 290 includes a rotor 222, 232, 242, 262 and 292, and raceway 224, 234, 244, 264, and 294 between which the corresponding tubing loop is positioned to control the passage and flow rate of the corresponding fluid.

Platelet divert valve assembly 302 receives platelet collector tubing 82 and platelet return tubing loop 146; plasma divert valve assembly 304 receives plasma collector tubing 92 and plasma return tubing loop 166; and RBC divert valve assembly 306 receives RBC return tubing loop 172 and RBC collector tubing, if provided. As noted above, each pair of tubing for collection or return of separated blood components is disposed in a predetermined spaced relationship within window 118 of cassette assembly 24, thereby facilitating loading relative to the corresponding divert value assemblies. Platelet divert valve assembly 302, plasma divert valve assembly 304 and RBC divert valve assembly 306 each include a rotary occluding member 308, 310 and 312 that is selectively positionable between stationary occluding walls 314 and 316, 318 and 320, and 322 and 324, respectively, for diverting fluid flow through one tubing of the corresponding pairs of tubings.

Inlet pressure sensor 326 and return pressure sensor 328 within pump/valve/sensor assembly 12 engage the first and second pressure-sensing modules 134 and 138 of cassette assembly 24 through openings 330 and 332 in the cassette mounting plate 210. Similarly, ultrasonic level sensors 334 and 336 (see also FIG. 4) engage the blood return reservoir 150 of cassette assembly 24 through openings 338 and 339 in the cassette mounting plate 210.

Figure 4:
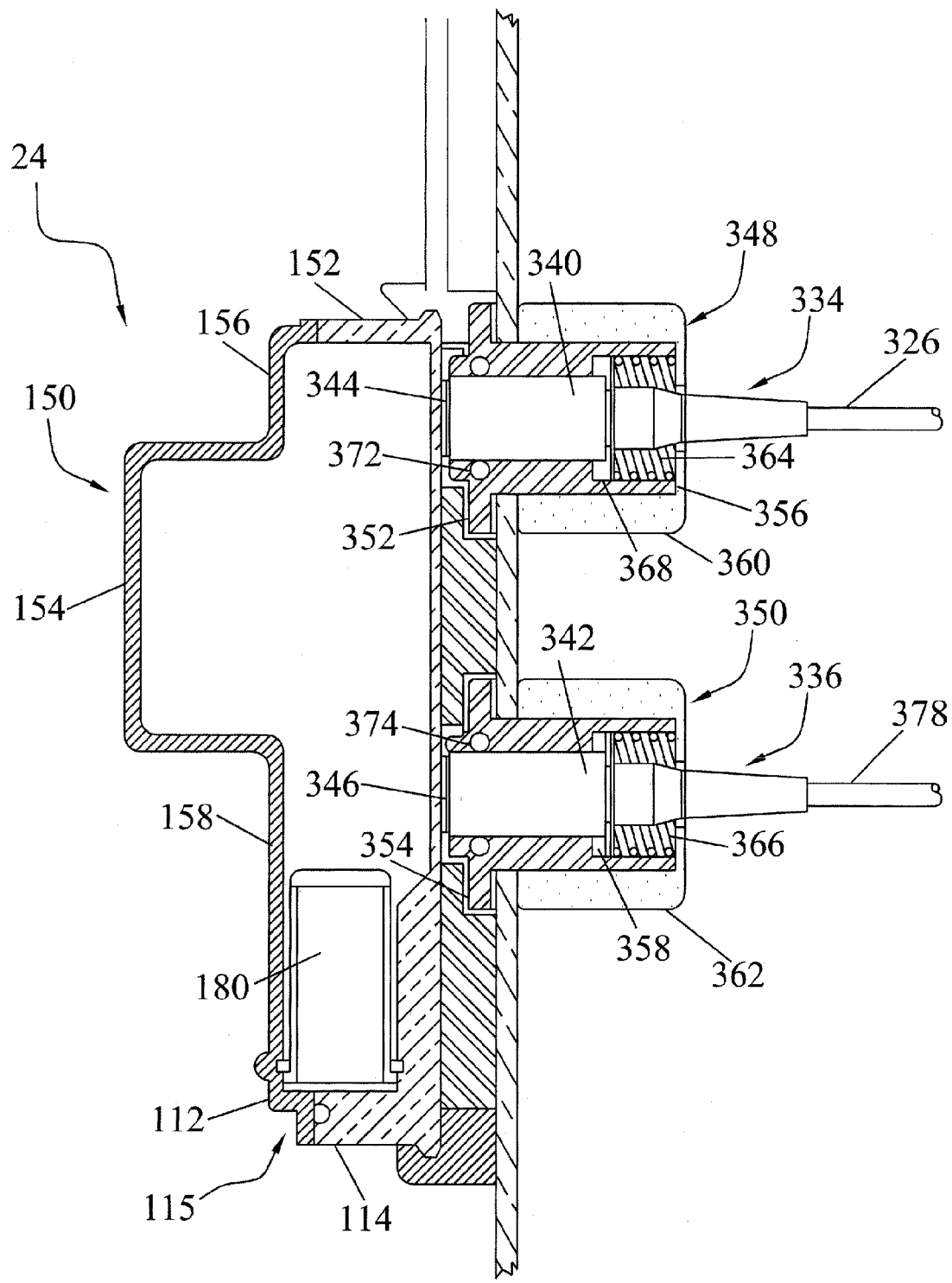
FIG. 4 is a cross-sectional side view of the upper and lower ultrasound sensors of the pump/valve/sensor assembly of FIG. 3 coupled with a reservoir of the cassette assembly of FIG. 2.

As shown in FIG. 4, when cassette assembly 24 is mounted on pump/valve/sensor assembly 12, the ultrasonic level sensors 334 and 336 will be positioned to monitor the fluid level in the blood return reservoir 150. Upper ultrasonic level sensor 334 contacts the reduced top section 156 of blood return reservoir 150 and lower ultrasonic level sensor 336 contacts the reduced bottom section 158 of blood return reservoir 150.

Ultrasonic sensors 334, 336 each comprise pulse/echo transducers 340, 342 having a contact surface 344, 346 that facilitates divert dry coupling without a gel or other like coupling medium with the blood return reservoir 150. Ultrasonic sensors may comprise model Z-11405 transducers offered by Zevex Inc. of 5175 Greenpine Drive, Salt Lake City, Utah. Pulse/echo transducers 340, 342 are disposed within housings 348, 350 for connection with faceplate 200 of the blood component separation device 4. Housings 348, 350 include a flange 352, 354 for engaging the front of faceplate 200, and further include a threaded end 356, 358 that extends through the faceplate 200 to receive corresponding retaining nuts 360, 362. A slight clearance is provided for between flanges 352, 354 and faceplate 200. Springs 364, 366 are positioned within housings 348, 350 to act upon the corresponding pulse/echo transducers 340, 342 via E-clips 368, 370 disposed therebetween. Such spring loading of pulse/echo transducers 340, 342 yields a predetermined desired loading pressure for pulse/echo transducers 340, 342 relative to reservoir 150 during operation, for example, at least about 5 lbs. O-rings 372, 374 are provided intermediate pulse/echo transducers 340, 342 and housings 348, 350 to provide a sliding seal therebetween. Cables 376, 378 are connected to transducers 340, 342 to provide pulsing signals and return detected echo signals.

By gauging the presence and timing of return ultrasonic echo pulses each of sensors 334 and 336 can be employed to monitor the presence or absence of fluid within their corresponding echo regions within the blood return reservoir 150, and permit blood component separation device 4 to provide pump control signals in response thereto. More particularly, when return blood accumulates up into the echo region of upper level sensor 334 during blood processing, ultrasonic pulses emitted by upper level sensor 334 will readily pass through the return blood and reflect off of the opposing reservoir outside sidewall/air interface to yield echo pulses having a predetermined minimum strength that are detected by upper sensor 334 within a predetermined time period after transmission. When such echo pulses are received, upper sensor 334 provides a signal that is used by blood component separation device 4 to initiate operation of blood return pump 290 so as to remove accumulated return blood from the blood return reservoir 150 and transfer the same to the donor.

When blood return pump 290 has removed return blood from the reservoir 150 down into the lower echo region, ultrasonic pulses emitted by lower level sensor 336 will not be reflected at the opposing reservoir outside sidewall/air interface to yield echo pulses having a predetermined minimum strength for detection by lower level sensor 336 within a predetermined time period after transmission. When this occurs, lower level sensor 336 will fail to provide corresponding signals to blood component separation device 4, and blood component separation device 4 will automatically stop blood return pump 290 to stop further removal of return blood from the blood return reservoir 150, and return blood will again begin accumulating in reservoir 150. Thus, in the blood processing mode, blood component separation device 4 will not initiate operation of blood return pump 290 unless and until it receives signals from upper ultrasonic sensor 334, which signals indicate the presence of return blood in the upper echo region, and will thereafter automatically stop operation of blood return pump 290 if it fails to receive signals from ultrasonic sensor 336, which indicates the absence of return blood in the lower echo region.

In an initial saline prime mode, whole blood is introduced to reservoir 150 from a donor through blood return tubing 34, integral passageways 190a, 190b, and tubing loop 192 via reverse operation of blood return pump 290. When such whole blood accumulates up into the echo region of lower level sensor 336, ultrasonic pulses emitted by lower level sensor 336 will pass through the blood and reflect off of the opposing reservoir outside sidewall/air interface to yield echo pulses having a predetermined minimum strength that are detected by lower level sensor 336 within a predetermined time period after transmission. When such echo pulses are received in the blood prime mode, lower level sensor 336 provides a signal that is used by blood component separation device 4 to turn off blood return pump 290 and end the blood prime mode. Blood component separation device 4 then initiates the blood-processing mode.

Ultrasonic sensors 334, 336 can confirm the desired mounting relationship of cassette member 115 on cassette mounting plate 210. If the desired mounting has been achieved, the sensors 334, 336 should be coupled to reservoir 150 so that ultrasonic pulses reflect off the interface between the inside surface of the back sidewall of reservoir 150, which is the sidewall contacted by the sensors 334, 336 and contained air within reservoir 150, and be received with a predetermined minimum strength within a predetermined time period after transmission. If such echo pulses are received with respect to both ultrasonic sensors 334, 336, the desired loading relationship will be confirmed. Further, ultrasonic sensors 334, 336 may sense echo pulses from the interfaces between fluid contained within the reservoir 150 and the inside surface of the outer sidewall of reservoir 150 in the upper and lower echo regions of the reservoir during operation. If such echo pulses are detectible within predetermined time windows, corresponding signals provided by ultrasonic sensors 334, 336 can provide a further input for blood component separation device 4 to control operation of blood return pump 290.

In the illustrated arrangement, the upper and lower ultrasonic sensors 334 and 336 operate via coupling with reduced cross-sectional portions 156 and 158 of reservoir 150. The reduced upper and lower reservoir portions 154, 158 accommodate reliable detection of echo pulses when fluid is present in the upper and lower echo regions, and the enlarged midportion 158 provides satisfactory return blood holding capabilities.

In an initial blood prime mode of operation, blood return pump 290 is operated in reverse to transfer whole blood through blood removal/return tubing assembly 26, integral blood return passageway 190, blood return tubing loop 192 and into reservoir 150. Contemporaneously and/or prior to the reverse operation of blood return pump 290, anticoagulant peristaltic pump 220 provides anticoagulant from anticoagulant tubing assembly 50, through anticoagulant integral passageway 120, and into blood removal tubing 32 and blood return tubing 34 via manifold 38. When lower level ultrasonic sensor 336 senses the presence of the whole blood in reservoir 150 a signal is provided and blood component separation device 4 stops blood return peristaltic pump 290. During the blood prime mode blood inlet pump 230 is also operated to transfer blood into blood inlet integral passageway 130, through blood inlet tubing loop 132 and into blood inlet/blood component tubing assembly 28 to prime the blood-processing vessel 10.

During the blood prime mode, vent bag assembly 100 receives air from reservoir 150. The occluding members 308, 310, 312 of divert assemblies 302, 304, 306 are positioned to divert flow to the reservoir 150. It should also be noted that to facilitate blood priming, the cassette assembly 24 is angled upward at about 45° in its loaded position, and the integral passageways of cassette member 115 are disposed so that all blood and blood component inlet paths provide for a bottom-to-top flow.

In the blood processing mode, the blood inlet peristaltic pump 230, platelet peristaltic pump 240 and plasma peristaltic pump 260 operate continuously, and the occluding members 308, 310, 312 are positioned for collection or return of corresponding blood components, as desired.

During a blood removal submode, blood return peristaltic pump 290 is not operated so that whole blood will pass into blood removal/return tubing assembly 26 and to processing vessel 10 via the cassette assembly 24 and blood inlet/blood component tubing assembly 28. Uncollected blood components transfer from the processing vessel 10 to cassette assembly 24, and accumulate in reservoir 150 up to a predetermined upper level. When blood components reach the upper level ultrasonic sensor 334, the blood component separation device 4 ends the blood removal submode and initiates a blood return submode.

The blood return submode initiates forward operation of blood return peristaltic pump 290. The volume transfer rate of return blood through blood return tubing loop 192 utilizing blood return peristaltic pump 290, according to a predetermined protocol, is greater than the volume transfer rate through blood inlet tubing loop 132 utilizing blood inlet peristaltic pump 230. As such, the accumulated blood in reservoir 150 is transferred into the blood return tubing of blood removal/return tubing assembly 26 and back into the donor. When the accumulated return blood in reservoir 150 is removed down to a predetermined level, lower level ultrasonic sensor 336 will fail to provide signals, whereupon blood component separation device 4 will automatically stop blood return peristaltic pump 290 to end the blood return submode. This automatically serves to reinitiate the blood removal submode since blood inlet peristaltic pump 230 operates continuously.

During the blood processing mode, pressure sensor 326 senses negative or positive pressure changes within the blood removal tubing 32 of the blood return tubing assembly 26, via first integral blood inlet passageway 130a. Such monitored pressure changes are communicated to blood component separation device 4 which in turn controls blood inlet pump 230 and return pump 290 so as to maintain fluid pressures within predetermined ranges during the blood removal and the blood return submodes. Specifically during the blood removal submode, if a negative pressure is sensed that is less than a predetermined negative limit value, then blood component separation device 4 will slow down operation of blood inlet pump 230 until the sensed negative pressure is back within an acceptable range. During the blood return submode, if a positive pressure is sensed that exceeds a predetermined positive limit value, then blood component separation device 4 will slow down operation of blood return pump 290 until the sensed positive pressure is back within an acceptable range.

Pressure sensor 328 monitors the positive pressure within the second integral blood inlet passageway 130b and blood inlet tubing 62. If such sensed positive pressure exceeds a predetermined maximum value, blood component separation device 4 will initiate appropriate responsive action, including, for example, slowing or stopping the centrifuge and peristaltic pumps.

During the blood-processing mode, blood component separation device 4 controls the operation of anticoagulant pump 220 according to a predetermined protocol and responds to signals provided by AC sensor 340, such as, indicating a depleted anticoagulant source. Also, blood component separation device 4 controls the operation of divert assemblies 302, 304, 306 according to predetermined instructions and further pursuant to any detect signals provided by RBC spillover detector 342. In the latter regard, if an RBC spillover in the separated platelet stream is detected, blood component separation device 4 will automatically cause occluder member 308 to divert the separated platelet stream to the return reservoir 150 until the RBC spillover has cleared, thereby keeping red blood cells from undesirably passing into platelet collector tubing assembly 80.

In normal operation, whole blood will pass through needle assembly 30, blood removal tubing 32, cassette assembly 24 and blood inlet tubing 62 to processing vessel 10. The whole blood will then be separated in vessel 10. A platelet stream will pass out of the vessel, through platelet tubing 66, back through cassette assembly 24, and will then be either collected in collector assembly 80 or diverted to reservoir 150. Similarly, separated plasma will exit vessel 10 to plasma tubing 68 back through cassette assembly 24, and will then either be collected in platelet tubing assembly 90 or diverted to reservoir 150. Further, red blood cells, plasma, and, potentially, white blood cells will pass out of vessel 10 through RBC tubing 64, through cassette assembly 24 and into reservoir 150. In this regard, it is contemplated that second spur 170b of integral passageway 170 may be connected to a separate RBC collector tubing assembly (not shown) and RBC divert valve assembly 306 could be operated for the collection of RBC.

As noted above, when uncollected platelets, plasma, RBC, aid, potentially, white blood cells have accumulated in reservoir 150 up to upper ultrasonic level sensor 334, operation of return peristaltic pump 290 will be initiated to remove the components from reservoir 150 and transfer them back to the donor via the return tubing 34 and needle assembly 30. When the fluid level in the reservoir 150 drops down to the level of the lower ultrasonic level sensor 336, the return peristaltic pump 290 will automatically turn off re-initiating the blood removal submode. The cycle between blood removal and blood return submodes will then continue until a predetermined amount of platelets or other collected blood components have been harvested.

Reservoir 150 and upper and lower ultrasonic sensors 334 and 336 are provided so that, during the blood processing mode, approximately 50 milliliters of return blood will be removed from reservoir 150 during each blood return submode and accumulated during each blood removal submode. In such embodiment, lower and upper level triggering by ultrasonic sensors 334 and 336 occurs at fluid volumes of about 15 milliliters and 65 milliliters, respectively, within reservoir 150. For such embodiment, it is also believed desirable to provide for a volume transfer operating rate range of about 30 to 300 milliliters/minute through blood return tubing loop 192 utilizing return pump 290, and a volume transfer operating rate range of about 20 to 140 milliliters/minute through blood inlet tubing loop 132 utilizing inlet pump 230. Additionally, for such embodiment a negative pressure limit of about −250 mmHg and positive pressure limit of about 350 mmHg is believed appropriate for controlling the speed of inlet pump 230 and return pump 290, respectively, in response to the pressures sensed in first pressure sensing module 134. A positive pressure limit of about 1350 mmHg within second sensing module 138 is believed appropriate for triggering slow-down or stoppage of the centrifuge and pumps.

In many blood separation devices, the accuracy and precision of the pumps affect the efficiency of the blood separation process. Not only is there likely to be some variation between the pumps themselves, but also each procedure requires a new disposable set, which is mounted, with slight variation, on the separation device. Each variable contributes to stroke-volume variation between pumps of as much as plus or minus 6%. Often these inaccuracies are compensated for by under pumping, that is, by pumping as if the pump volume were at the high end of its range, and by using multiple scales to check the weight of fluids being added, lost or collected. The efficiency of the blood separation process can be improved and certain expensive components eliminated if the pumping ratios of the pumps can be determined. By alternately filing and emptying the reservoir 150 to replicable levels detected by the ultrasonic level sensors 334, 336 pumping ratios between any or all of the pumps can be determined. These ratios can then be used to adjust the control of the blood separation process. A ratio test may be performed before actual blood processing begins or during blood processing. The ratio test may also be preformed once or multiple times during a single blood separation process.

Since a reservoir 150 is part of the removable and disposable cassette 24, the volume of any particular reservoir is known only approximately. Moreover, placement of the reservoir 150 over the sensors 334,336 is not necessarily precise. Most importantly, the ultrasonic sensors themselves are subject to considerable variation. In the type of sensors identified above, the functional sensing element is relatively small but is mounted in a housing with a potting material. The functional element may, therefore, be anywhere within the region filled with the potting material. If the housing were rotated within its mounting socket, the location of the functional element with respect to the reservoir 150 would change. In any case, the linear distance between the functional elements on the sensors 334, 336 on different blood separation devices must be expected to be different. On the other hand, the distance between the functional elements of the sensors 334, 336 on any particular device may be expected to be consistent and the detecting of a fluid level in the reservoir may be expected to be very precise. This allows the control system, using the process or processes described below, to determine the pump volume ratios for any or all pumps. To increase the accuracy, it is important that hysteresis effects be reduced by consistently detecting the fluid level as the fluid level is moving in the same direction, thus allowing sensing at the same edge of the functional sensing element each time.

Overall procedures for processing blood are known in the art, and many different procedures or processes may be used in connection with this invention, depending, for instance, on the type of blood products collected from or returned to the donor. For example, processing steps are known from U.S. patent application Ser. No. 09/797325. Use of a computing and data retrieval assembly is shown in more detail in U.S. Pat. Nos. 5,496,265; 5,658,240; 5,712,798; and 5,970,423, all of which being commonly assigned to the assignee of the present invention, the disclosures of which being incorporated herein in their entireties, as if fully set forth here by this reference thereto.

In such known blood-processing procedures, a system controller, usually comprising one or more microcomputers and associated software, controls the flow of blood and other fluids by activating pumps for a selected number of pump cycles. If the stroke-volume ratios of the pumps are accurately determined, any of the known processes may be optimized by accurately specifying numbers of revolutions of the various pumps to draw blood, mix fluids such as anti-coagulant, or return blood components to the donor or patient. The processes described herein may be added as a subroutine to any such blood-processing procedure.

Figure 5:
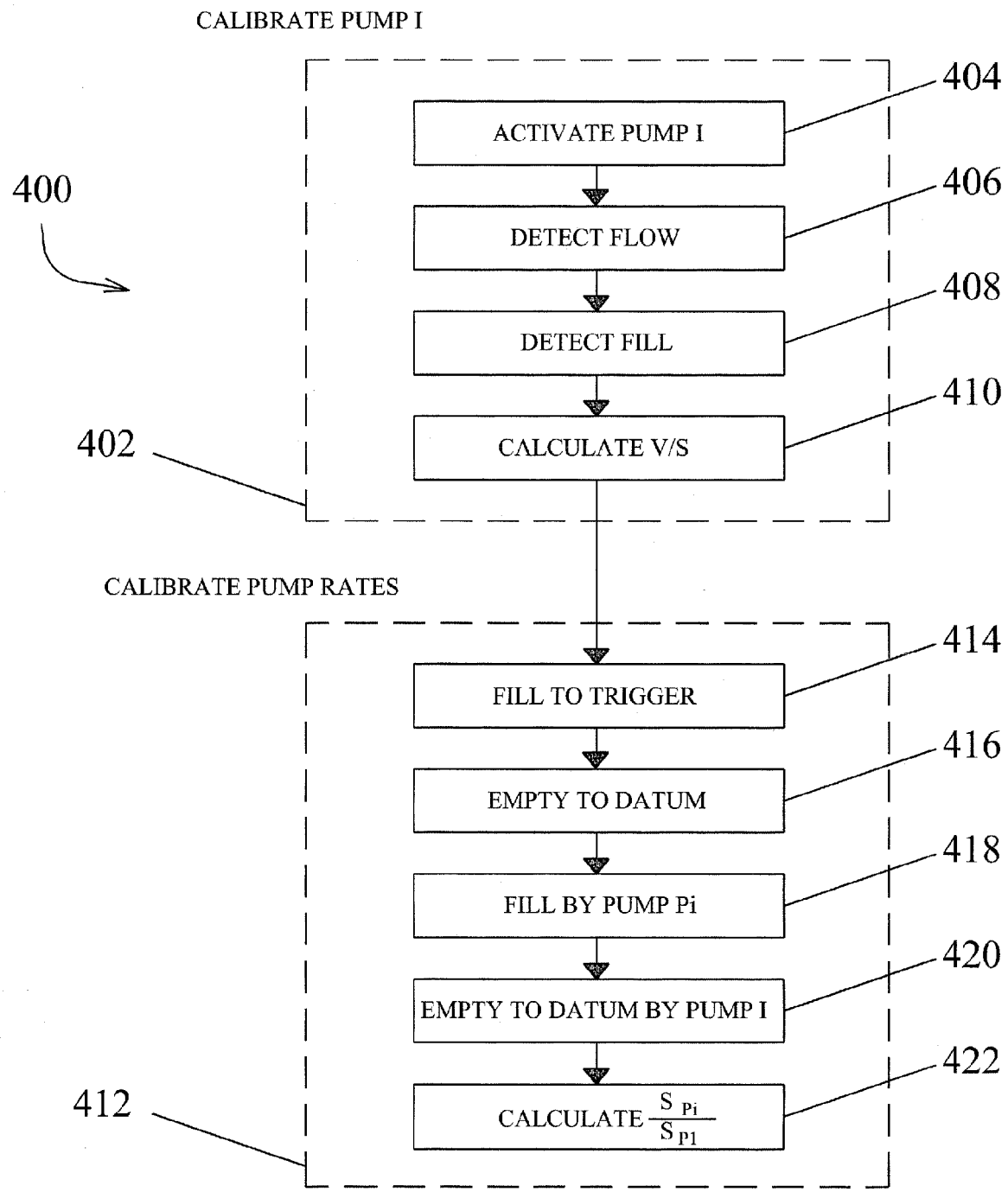
FIG. 5 is a flow chart illustrating the general process for pump balancing in the apheresis system.

FIG. 5 shows a general structure of a pump-balancing subroutine 400. Initially, a master pump, Pump I, is calibrated 402. This may be any of the pumps in the system capable of influencing the fluid level in the reservoir 150. Most commonly, this would be the return pump 292. Pump I is activated 404 until flow is detected 406 at the lower ultrasonic sensor 336. The fluid level in the reservoir is raised above the sensor by an arbitrary amount and then flow is reversed, or the reservoir is allowed to drain until the fluid level reaches the bottom of the sensor, called hereafter a "datum", thus detecting a filled condition 408 at the datum. If the volume of the reservoir is known, it is possible to calculate 410 an actual stroke volume, that is, a value for fluid volume per stroke or revolution of the pump. To determine ratios of stroke volumes between particular pumps, however, the actual volume of the reservoir need not be known. In fact, it is assumed that there would be variation between reservoirs in different disposable sets, and between the configurations of sensors on different machines. Thus it is unlikely that the volume of a particular reservoir between a particular set of sensors would be known. To determine ratios, it is only necessary that a replicable volume be added to or emptied from the reservoir. In would be apparent, for example, that an upper sensor 334 could be used instead of the lower sensor 336, and the fluid level could be lowered below the upper sensor by a selected number of pump revolutions and then raised back up to the upper sensor. This type of operation would in no way depart from the teachings set forth herein.

After the first pump, Pump I, has been calibrated, the remaining pumps can be calibrated 412 with respect to Pump I. The reservoir is primed to assure consistent initial conditions by filling 414 the reservoir at least above the bottom sensor, for example to the trigger or upper sensor. The reservoir is allowed to empty 416 to the datum, that is, until the fluid level reaches the bottom of the lower ultrasonic sensor 334. Pump I is used to fill 418 the reservoir by a replicable amount. This may be done by activating Pump I for a predetermined number of revolutions or strokes. The action of Pump I is then halted and the selected test pump $P_i$ empties 420 the reservoir to the datum. Given the number of strokes from each pump to fill and empty the same volume, it is possible to calculate 422 a ratio $S_{Pi}/S_{PI}$, which compares the action of the selected pump $P_i$ to the master pump $P_I$. This test will ordinarily be run during the priming cycle of the apparatus, before blood processing begins. For each pump, the test may be run several times in order to obtain a statistically significant sample, improving the accuracy of the measurements. Once ratios have been measured for all desired pumps, comparing those pumps to the master pump, any two ratios may be combined, and a new ratio may be computed that compares the two selected pumps to each other and eliminates reference to the master pump, Pump I.

The measured ratios, which are unique to the disposable set, blood processing apparatus and set-up conditions, can then be used in the blood processing protocol instead of the approximations usually used to control the action of the pumps that withdraw blood, add anti-coagulant, direct blood to the vessel for separation, store components and return other blood components to the donor. As is known in the art, peristaltic pumps may be driven at selected times and for selected numbers of revolutions to combine fluids is desired proportions. For example, blood withdrawn from the donor may be mixed with at least a pre-determined portion of anti-coagulant to prevent blood clotting in the device. Because of uncertainty in the action of the pumps, prior protocols have delivered excess anti-coagulant, for example, to assure that at least the necessary minimum anti-coagulant was mixed with a volume of blood. This was accomplished by specifying a first number of revolutions of a pump delivering blood and a second number of revolutions of a pump delivering anti-coagulant in the control software of the apparatus. These first and second numbers, for example, can now be set more accurately using the ratios determined with this apparatus and method.

The general process described above is implemented in greater detail in the algorithm shown in FIGS. 7A through 11B. A similar program structure is suggested for each of the steps or subroutines mentioned above. As a shared programming style, the subroutines described hereafter generally comprise a pre-enter section, which establishes common parameters and pre-conditions for the subroutine. A pre-process section then runs continually at a relatively slow cycle rate, checking that the general conditions for performing a test or procedure are maintained while the subroutine is running. At the same time, a test or procedure called a "Proxy" is run at a relatively high cycle rate to detect the desired condition or change of condition for the particular part or section of the program and communicate that condition to the main process control program. After the condition is detected, a post-exit section resets the variables or parameters, preparatory to the next subroutine of the program.

Figure 6A:
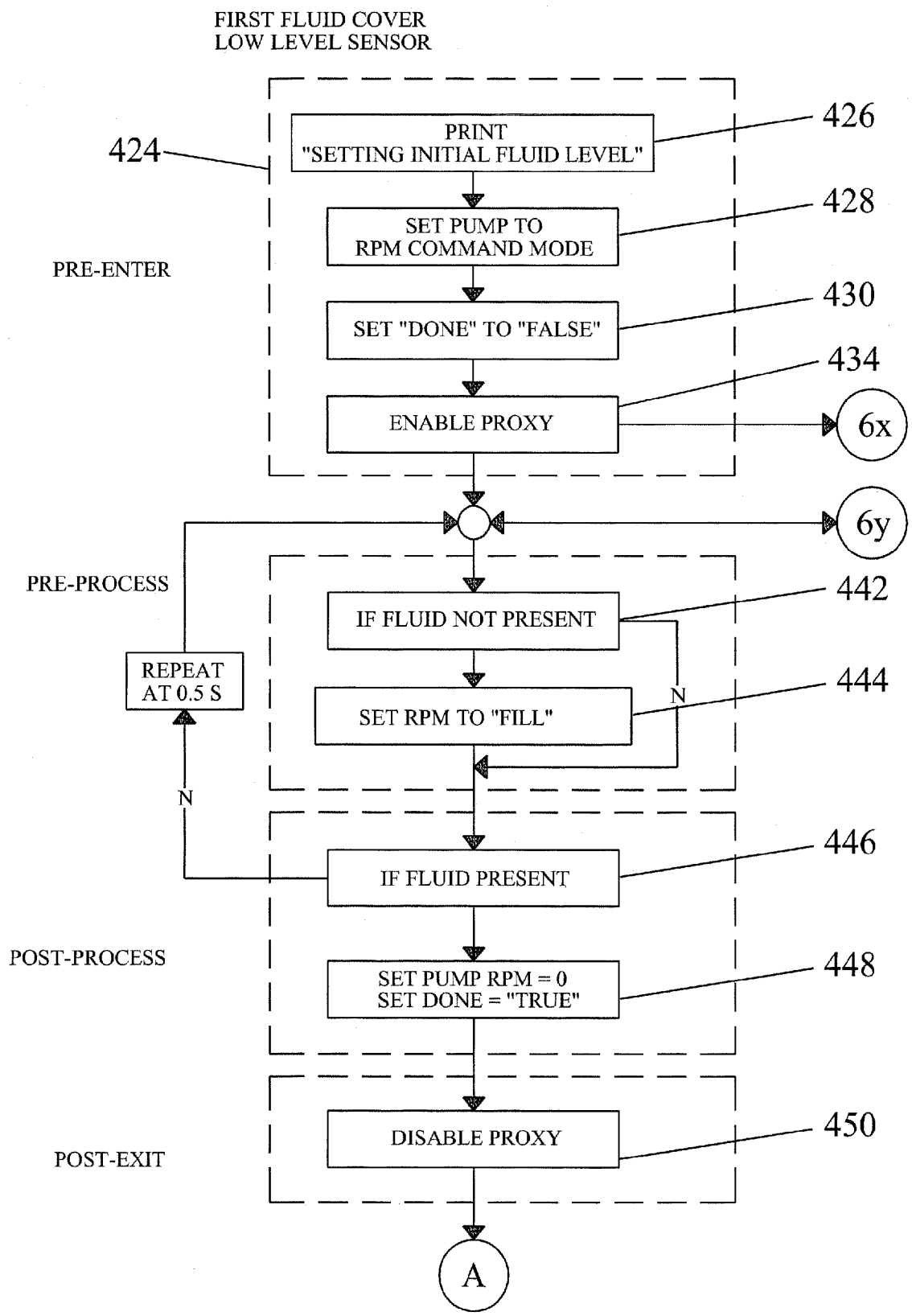
FIG. 6A and FIG. 6B comprise a flow chart of a subroutine for detecting a low level sensor.
Figure 6B:
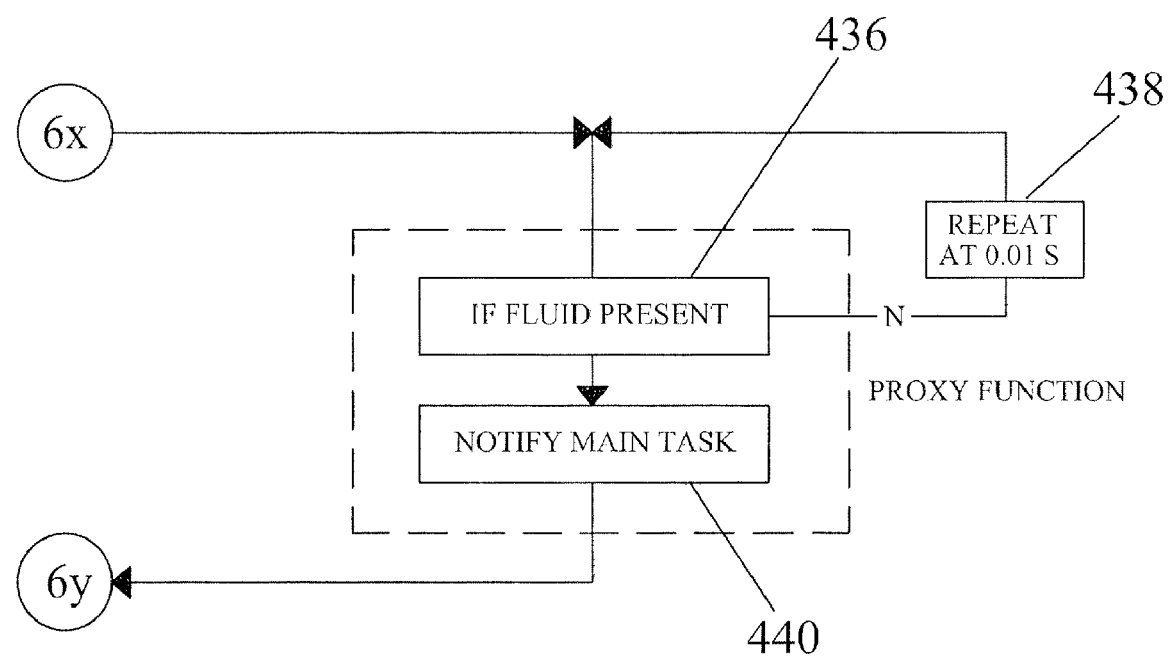

Initially, as shown in FIGS. 6A and 6B, the lower ultrasonic or low level sensor 336 should be covered with fluid, for example, with saline for priming or with blood. A pre-enter process 424 sets the initial state of variables. Optionally, a statement "Setting Initial Fluid Level" may be printed 426 or communicated either to the machine operator or to other programs controlling the apheresis machine. The program sets 428 the initial speed of Pump I to a selected number of revolutions per minute. A "Done" flag is set 430 to false, and the "Proxy" routine is enabled 432, that is, the principle test for this subroutine begins to cycle at a relatively high rate. If the disposable is not already filled with fluid, fluid is pumped into the reservoir until fluid is detected 436 at the low level sensor. The sensor attempts 438 to detect fluid at a rate of once every 0.01 seconds or 100 cycles per second until fluid is detected. The main program is notified 440 as soon as the desired condition is detected.

At the same time, the program monitors certain conditions necessary for a valid test. This monitoring is also performed cyclically, but at a slower rate. If there is 110 fluid present 442 in the disposable, the pump begins to fill 444 the reservoir, and this status is communicated to the other programs or to the operator. This process proceeds at a cyclic rate of once every 0.5 seconds, that is, twice per second, until fluid 446 is detected at the low lever sensor. Notification from the proxy 440 will cause the process to cycle before the next 0.5 second interval, insuring that the fluid level state change is responded to quickly. When fluid is detected, the pump is stopped 448, the "Done" flag is set to "true", and the state is communicated. The Proxy function can then be disabled 450, that is, the cyclic test of steps 436, 438 and 440 can be stopped.

Figure 7A:
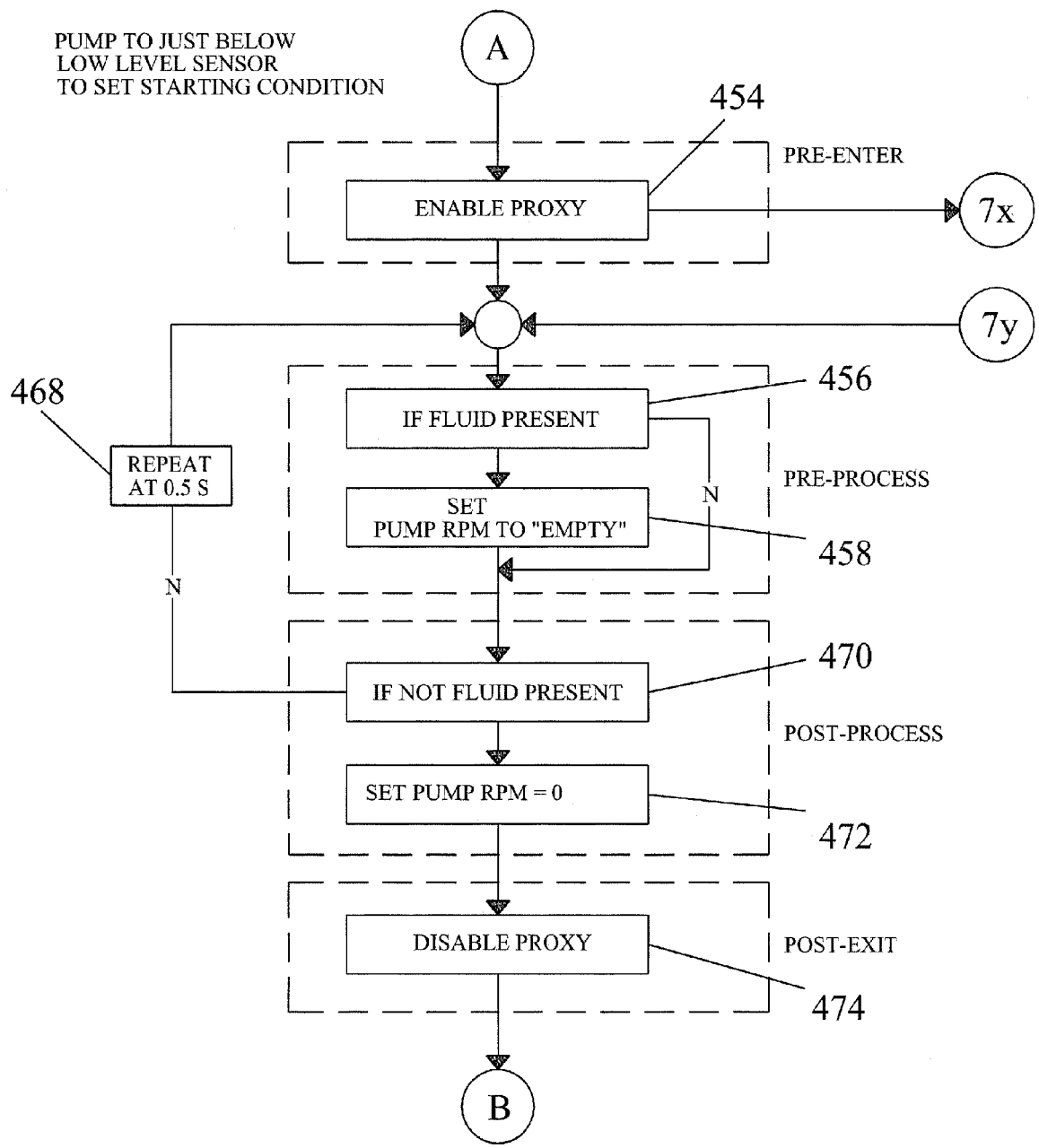
FIG. 7A and FIG. 7B comprise a flow chart of a subroutine for setting a starting condition.
Figure 7B:
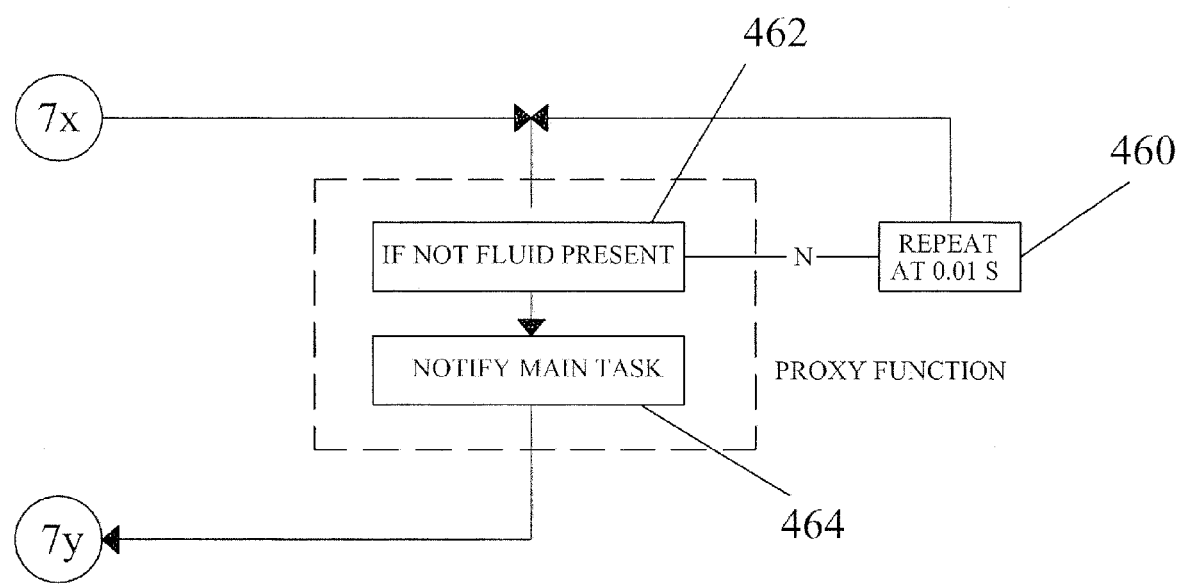

Next, as shown in FIGS. 7A and 7B, the fluid in the reservoir is lowered to just below the low level sensor, preparatory to filling the reservoir. Approaching this datum or starting condition from the same direction each time the algorithm is used, that is, from above or by lowering the fluid level, increases the accuracy of the process by eliminating a hysteresis effect. The Proxy function for this program segment is enabled 454, that is, it begins to run repetitively. The program checks 456 that the low level sensor is covered with fluid. If it is, the pump begins to empty 458 the reservoir. With the pump emptying the reservoir, the program rapidly samples the sensor at a rate of one sample every 0.01 seconds, that is, one hundred samples per second 460 until the sensor no longer detects fluid 462. This is the "Proxy" or principle test of this subroutine. The subroutine notifies 464 the main program and stops.

In a parallel process, but at the slower rate 468 of once every 0.5 seconds, that is, two times per second, the program re-checks 470 for fluid at the low level sensor, and stops 472 the pump if fluid is not present. If the fluid level drops below the low level sensor, the Proxy function is disabled 474. Again, notification from the proxy 440 will cause the process to cycle before the next 0.5 second interval, insuring that the fluid level state change is responded to quickly.

Figure 8:
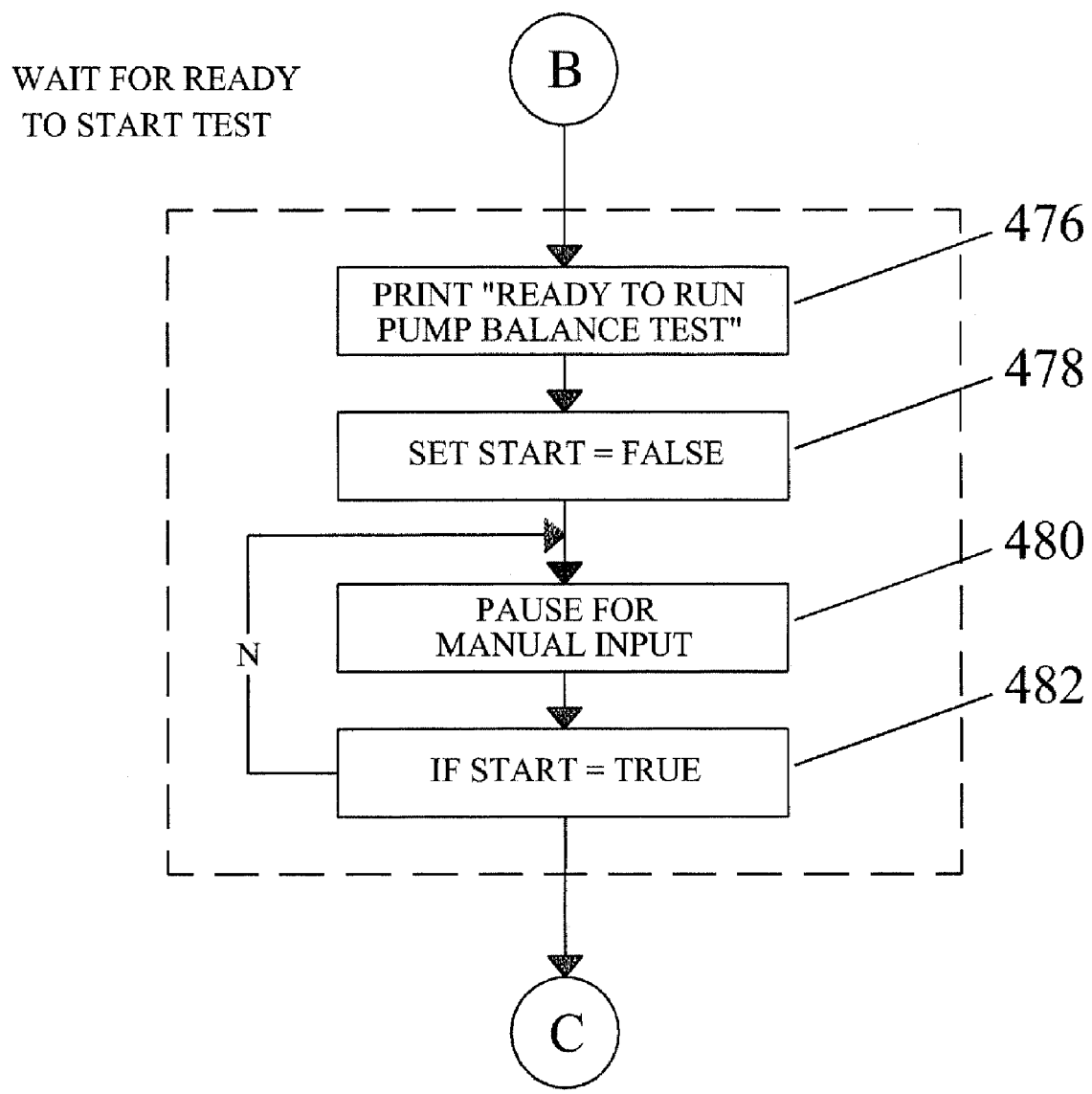
FIG. 8 is a flow chart of a subroutine for waiting for a start test signal.

As a test option, it is possible to pause for operator authorization to continue the calibration test, as illustrated in FIG. 8. The program communicates 476 to the operator a message such as "Ready to run pump balance test". A "Start" flag is set 478 to "false", and the program pauses 480, waiting for manual authorization to proceed. When a signal is received, setting the "Start" flag to true 482, the program is authorized to proceed with the test. This pause for operator input is unnecessary, but may be useful during initial testing of a pump test program.

Figure 9A:
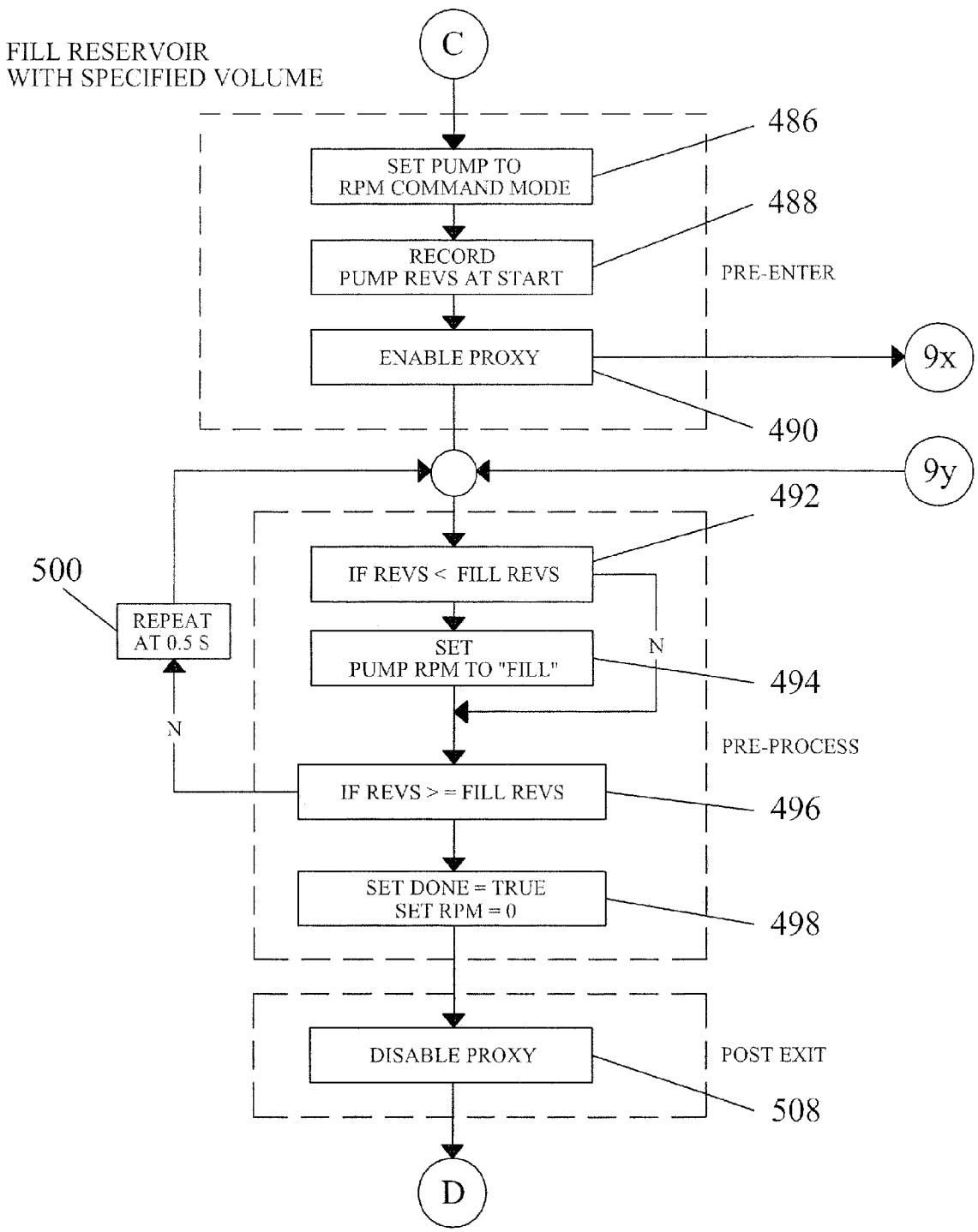
FIG. 9A and FIG. 9B comprise a flow chart of a subroutine for filling the reservoir.
Figure 9B:
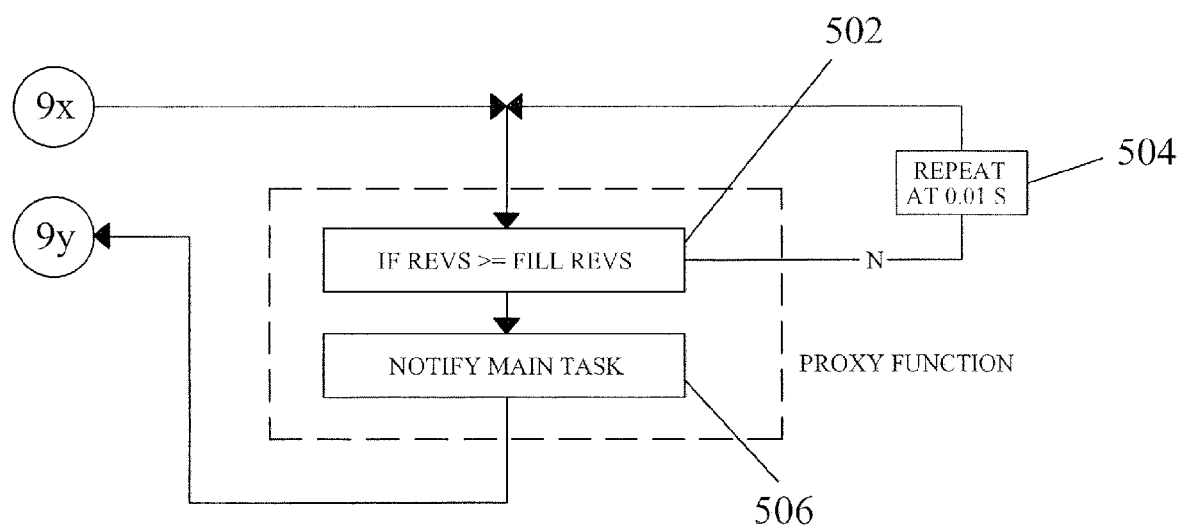
Figure 10A:
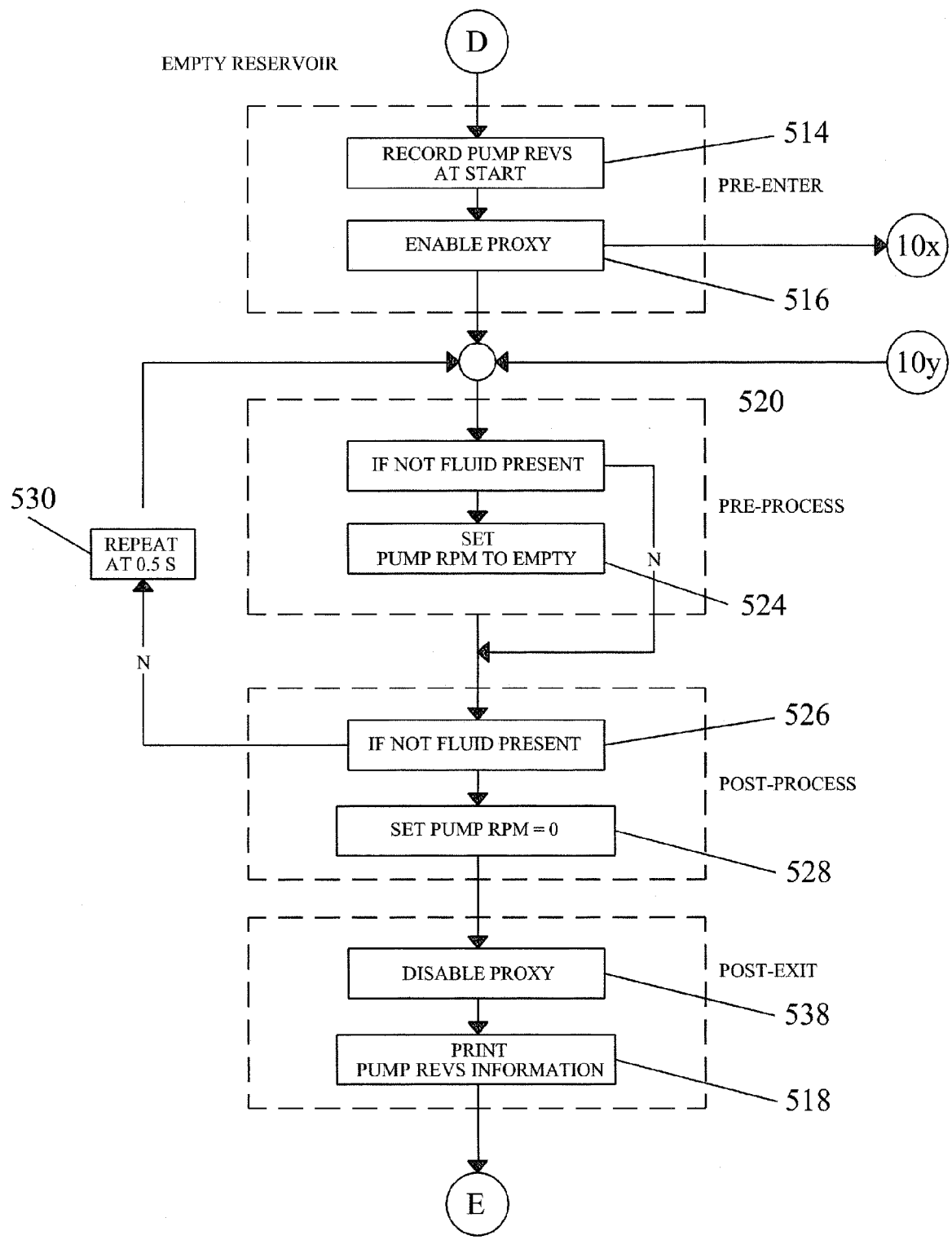
FIG. 10A and FIG. 10B comprise a flow chart of a subroutine for emptying the reservoir.
Figure 10B:
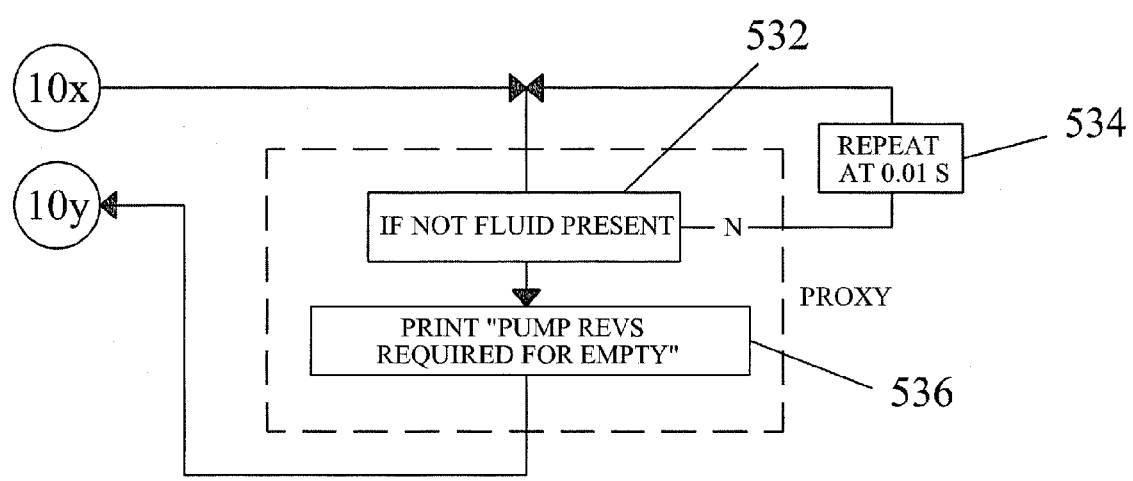

The next subroutine of the program, illustrated in FIGS. 9A and 9B, fills the reservoir to a replicable volume by activating a selected initial pump, Pump I, for a selected number of revolutions. The actual volume may not be known in milliliters, but because the volume can be precisely replicated, it can be used to determine ratios of pump stroke volumes between the different pumps of the apheresis machine. Beginning this subroutine, the speed and number of revolutions of Pump I is set 486. The start condition of Pump I is recorded 488, and the Proxy routine is enabled 490. If the number of revolutions of Pump I are less 492 than the pre-selected number of fill revolutions, then Pump I continues to fill 494 the reservoir. If the number of revolutions is greater than or equal to the number of fill revolutions 496, then a "Done" flag is set to "true" and Pump I is stopped 498. This portion of the subroutine is repeated 500 at a rate of about once every 0.5 seconds.

Meanwhile, in parallel, the Proxy routine tests 502 the elapsed number of revolutions from the start of the fill procedure. If the elapsed number is less than the pre-selected number of fill revolutions, the test is reiterated 504 at a rate of about once every 0.01 seconds, that is, one hundred samples per second. When the elapsed number of pump revolutions reaches the pre-selected number, the main program is notified 506 that the reservoir has been filled and the pump is stopped. The Proxy routine is disabled 508 in preparation for the next subroutine of the program.

The reservoir having been filled using the calibration pump (Pump I), the reservoir is now emptied using any of the remaining pumps, thereby providing a ratio of the number of revolutions of Pump I to fill the reservoir compared to the number of revolutions of the selected pump to empty the reservoir. With a complete set of ratios comparing Pump I to all other pumps, ratios of any selected pump to any other selected pump can be calculated. This final subroutine of the program, illustrated in FIGS. 10A and 10B, empties the reservoir by activating a selected pump, $P_i$, until the fluid level drops to immediately below the low level sensor. Beginning this subroutine, the speed and direction of revolutions of pump $P_i$ is set 514. The Proxy routine for this subroutine is enabled 516. A message reporting the number of revolutions of pump $P_i$ may be displayed 518 to the operator. The program checks 520 that fluid is still present at the low level sensor, and then instructs the pump $P_i$ to begin to empty the reservoir. The pump $P_i$ is started 524. If the low level sensor continues to detect fluid 526, then pump $P_i$ continues to fill the reservoir. Otherwise, the pump $P_i$ is stopped 528. This portion of the subroutine is repeated 530 at a rate of about once every 0.5 seconds.

Meanwhile, in the parallel Proxy routine, the program tests 532 the low level sensor for the presence of fluid. If fluid is detected, the test is re-iterated 534 at a rate of about once every 0.01 seconds. When fluid is no longer detected, the pump is stopped. A message may be generated, noting the number of revolutions needed to empty the reservoir 536, and this information is communicated to the main program. The program may be repeated for each remaining of the pumps of the apparatus. When completed, the Proxy cycle is disabled 538. For development purposes, the pump revolution data from both filling (FIG. 9A) and emptying (FIG. 10A) may be displayed 518 to the operator.

The calibration process described above generally would be performed during priming of the apparatus, when the pumps can be selectively driven without regard to an ongoing process of acquiring blood, separating the blood into components, and returning selected components, a process that requires the activation of various pumps at different times. Although the calibration process can be accomplished in a relatively short time, it nevertheless adds some time to the blood donation procedure. Moreover, it may become apparent that re-calibration may be needed during an apheresis procedure, because of some change affecting the apparatus, fluids or donor. It may be desirable, therefore, to generalize the calibration algorithm so that calibration may be performed during blood processing. During normal operation, pumps other than the return pump (Pump I) are operated continuously. The return pump 292 is controlled by allowing the reservoir to fill to a certain level with the return pump 292 off. The return pump is then started to empty the reservoir. The revolutions of Pump I and all other pumps would be counted during the filling and emptying cycle. A sequence of Fill/Empty cycles would be performed, with each cycle using an adjusted flow for a different pump $P_i$, thereby creating a set of linearly independent equations. The resulting set of equations can then be solved to provide ratios of stroke volumes comparing any of the pumps. Alternatively, changes to pump flows required by the apheresis protocol can be used to collect the required data for the equation set, rather than using flow changes performed only for the purpose of calibration.

An intra-process pump balance test is illustrated in FIGS. 11A through 11D. As the intra-process test starts, it may alert 540 the operator with a message, and begin initializing. A "First Full Cycle" flag is set 542 to false and an initial check of the low level sensor is made 544. If fluid is detected at the sensor, a "Refill" flag is set 546 to "false." Otherwise, the Refill flag is set 548 to "true" and a refill timer is started. The pump speed is selected 550 and the "Done" flag is "false" 552. The Proxy routine for this program segment is enabled 554 and begins cycling, as will be described below.

With initialization completed, the inter-process program performs pre-process tasks, which are generally repeated at intervals of 0.5 seconds in parallel with the Proxy routine. The program checks 558 for the conditions Not Refill and No Fluid at the low level sensor. If there is neither fluid nor a previous refill, the program sets the Refill flag to "true". The accumulated revolutions of the pumps from the cycle are recorded 566 and may be reported to the operator. The starting pump revolutions for the current cycle are recorded 568.

Figure 11A:
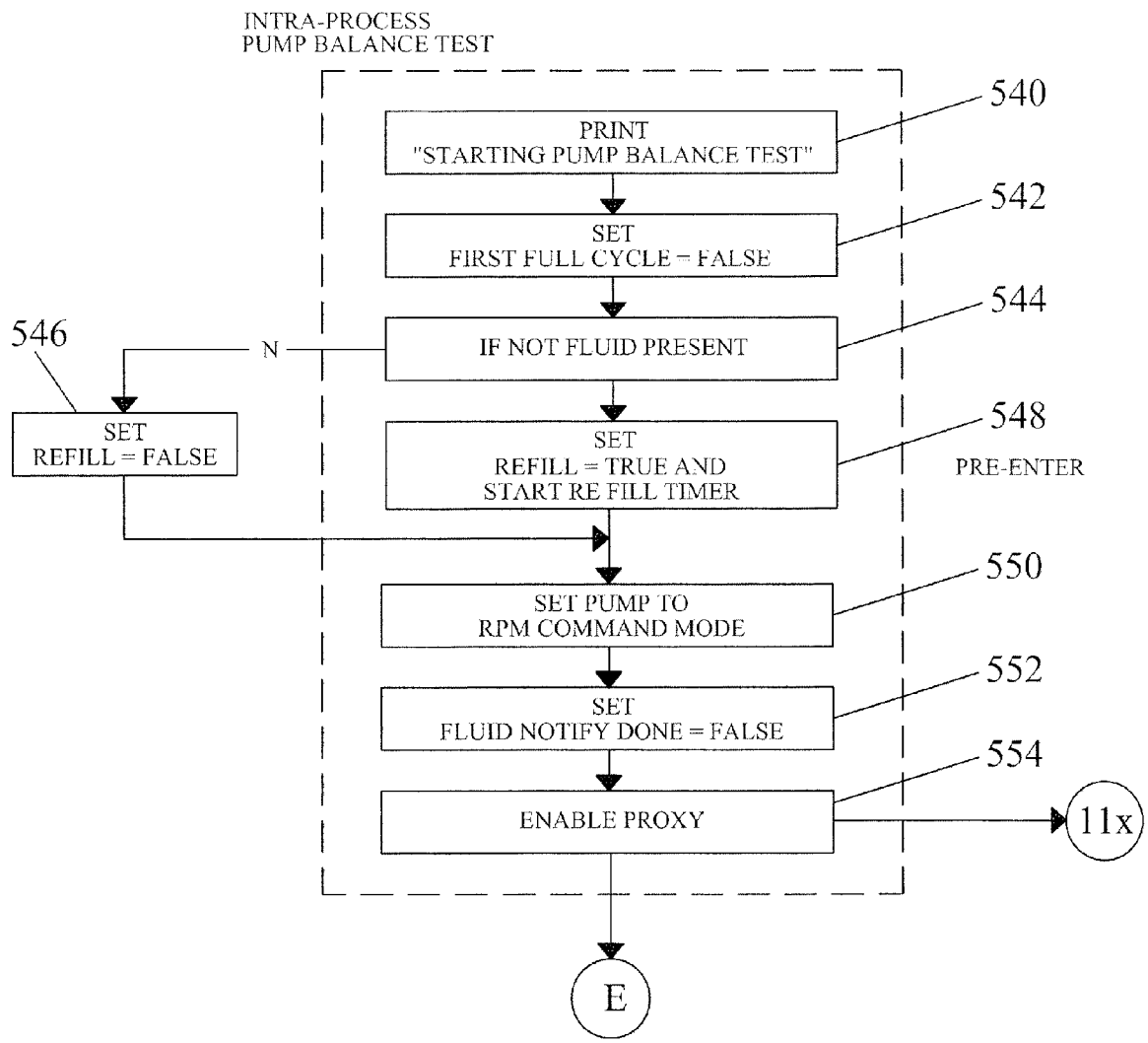
FIG. 11A, FIG. 11B, FIG. 11C and FIG. 11D comprise a flow chart for an intra-process pump balance test.
Figure 11B:
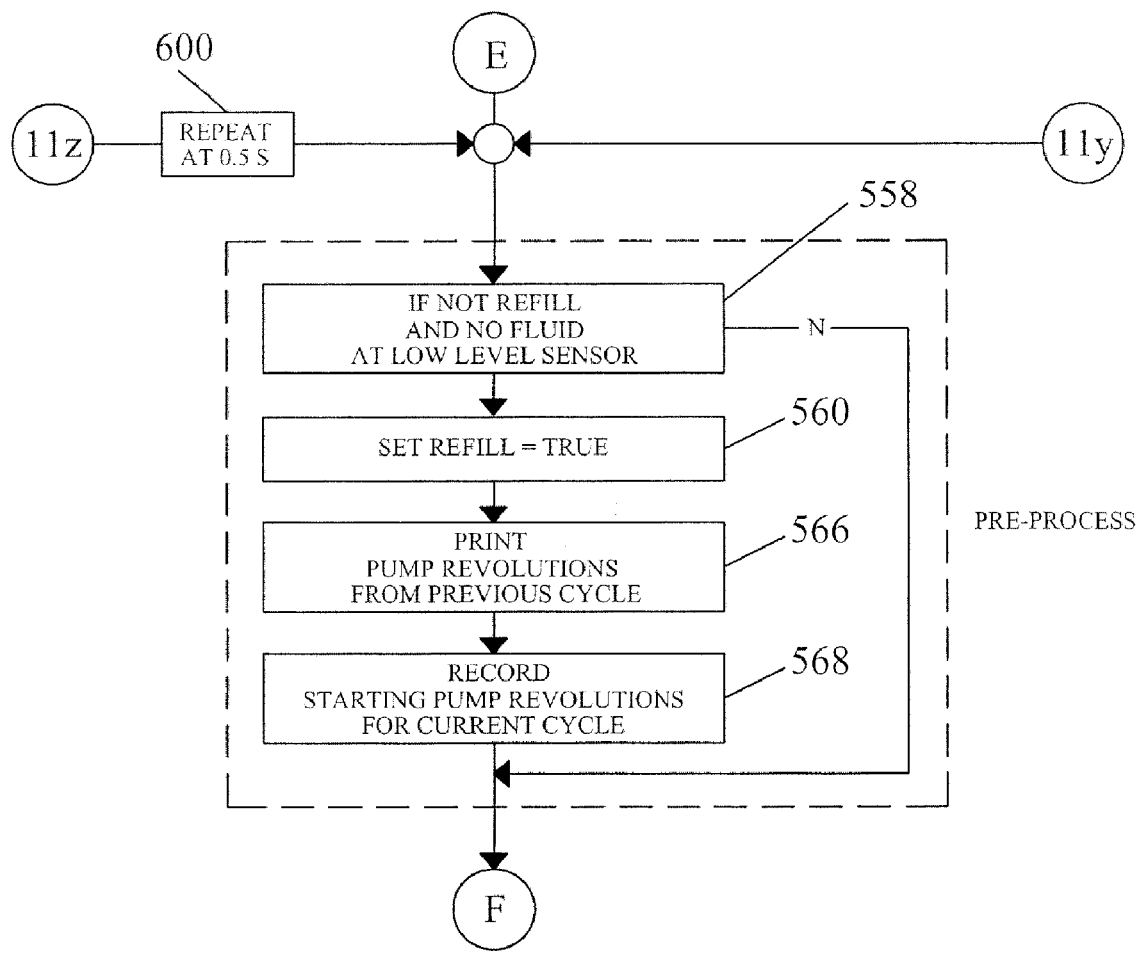
Figure 11C:
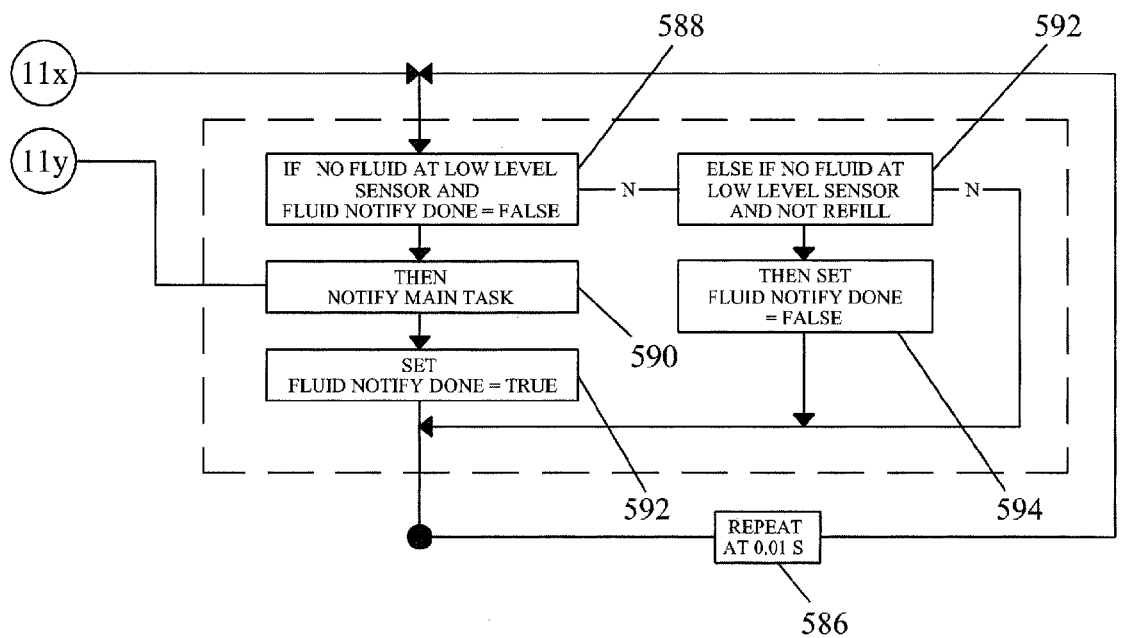
Figure 11D:
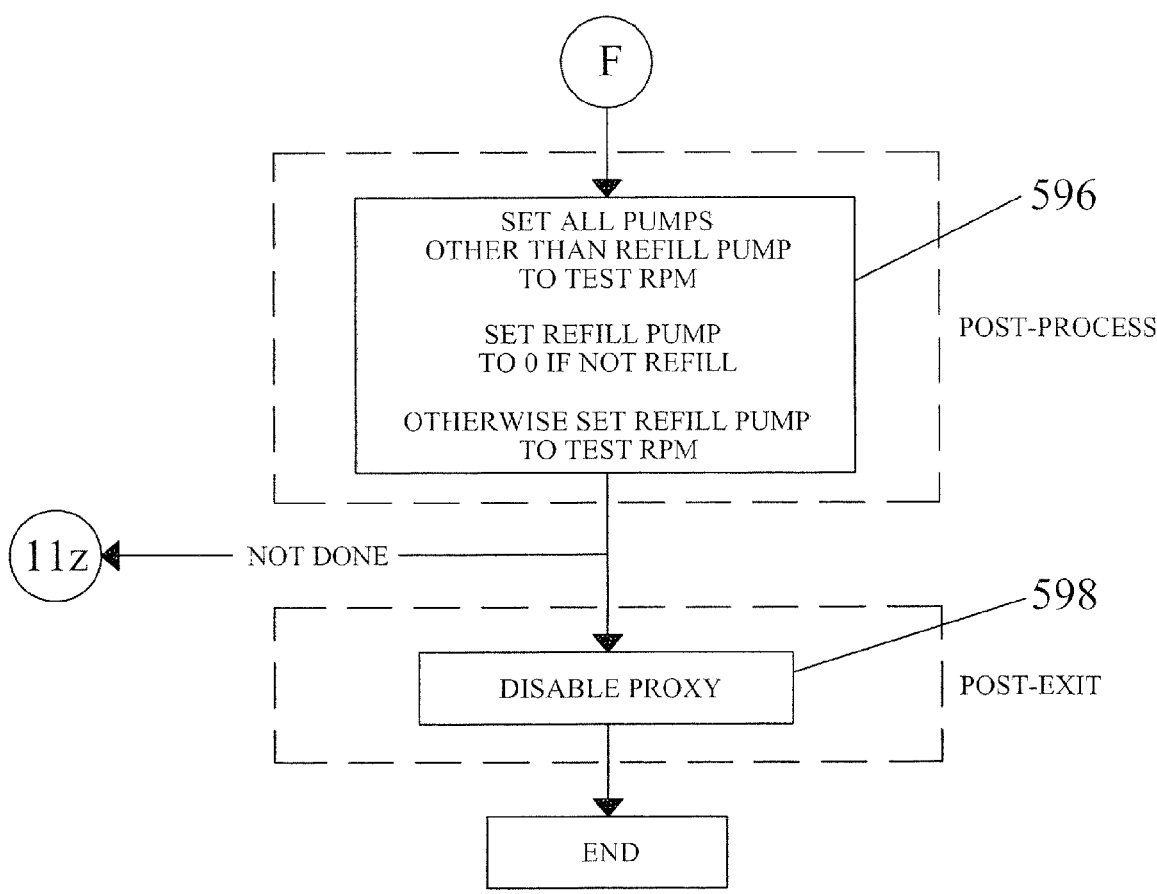

While the pre-process conditions exist, the Proxy function, illustrated in FIG. 11C, is performed in parallel at a rate 586 of one cycle every 0.01 seconds. In this case, the Proxy function determines when the additional fluid has been removed from the reservoir and reports the number of cycles of each of the pumps. The intra-process test program interrogates the low level sensor at step 588. If no fluid is detected and if the Fluid Notify flag is "false", the program will transmit 590 data comprising the number of rotations of the pumps to the main control program of the blood processing apparatus. As mentioned above, this data comprises the coefficients of a linear equation, which can be solved, using known techniques, with other test data from similar tests to provide ratios of stroke volumes for all pumps in the system. The program next sets the Fluid Notify Done flag to "true" and exits the Proxy function. On the other hand, if no fluid is detected at the low level sensor and the Refill flag is not set 592, then the fluid notify flag is set to "false" 594 and the program exits the Proxy function. So long as fluid is detected at the low level sensor, the program cycles through these tests at the relatively high cycle rate of one hundred cycles per second, that is, one cycle every 0.01 seconds.

When either the pre-process conditions fail (tested 600 once every 0.5 seconds) or fluid has been reduced below the low level sensor (tested 586 once every 0.01 seconds), the intra-process test program re-sets the pump speeds 596. Pump I is set to a speed greater than demand for the main apheresis process by a selected number of revolutions and thus allowed to refill the reservoir. Then a selected pump $P_i$ is set to an increased number of revolutions over the demand of the main apheresis process. The Proxy function is disabled 598 and the intra-process test program is run for the new pump $P_i$. When sets of data have been acquired for each of the pumps compared to Pump I, the resulting equations can be solved for the stroke volume ratios.

The stroke volume ratios of the pumps, available either from the priming test or the intra-process test, or both, can be used to optimize the apheresis process being run by the apparatus. Because of the variation between machines, disposable tubing sets and other components, control programs for blood processing machines generally incorporate a generous "safety factor" and therefore provide more fluids, such as anti-coagulant, than is needed. In addition, less blood or blood component may be collected than is optimum for the donor or the particular collection process if the actual performance of the pumps is unknown. By determining the stroke-volume ratios of the pumps, the apheresis control process can be improved by delivering more accurate proportions of fluid in the various stages of a process or procedure.

It will be apparent to those skilled in the art that various modifications and variations can be made to the structure and methodology of the present invention without departing from the scope or spirit of the invention. Thus, it should be understood that the invention is not limited by the examples discussed in the specification. Rather, the invention is intended to cover modifications and variations provided they come within the scope of the following claims and their equivalents.

What is claimed is:

1. An apparatus for processing blood comprising
a blood processing path for conducting blood through said apparatus;
a plurality of pumps for controlling the flow of blood through said path;
at least one control circuit electrically coupled to said pumps and controlling the operation of said pumps;
a reservoir in said path, said reservoir configured to contain a fluid, wherein a fluid level of said fluid in said reservoir is variable;
vent means in fluid communication with said reservoir, said vent means allowing air to pass into and out of said reservoir;
a first sensor couple to said reservoir for detecting said fluid level within said reservoir and electrically connected to said control;
a computer programmed with a control program for performing a test of pump ratios between at least two of said pumps by causing a first pump to pump fluid in a first direction into said reservoir and a second pump to pump fluid in a second direction out of said reservoir and finding a ratio of the action of said first pump to said second pump.

2. The apparatus of claim 1 wherein said control program begins said test by raising said fluid level in said reservoir above said first sensor and thereafter lowering said fluid level to said first sensor.

3. The apparatus of claim 2 wherein said control program causes said first pump to raise said fluid level in said reservoir by operating for a pre-determined number of cycles.

4. The apparatus of claim 3 wherein said control program causes said second pump to lower said fluid level in said reservoir to said sensor to determine the number of cycles of said second pump need to remove the volume of fluid supplied to the reservoir by said first pump.

5. The apparatus of claim 4 wherein said control program performs said test for all pumps in said apparatus.

6. The apparatus of claim 5 wherein said control program performs said test for an initial pump compared to each of the remaining pumps in said apparatus.

7. The apparatus of claim 1 wherein said control program performs said test for all pumps in said apparatus.

8. The apparatus of claim 7 wherein said control program performs said test for an initial pump compared to each of the remaining pumps in said apparatus.

9. The apparatus of claim 1 wherein said control program performs said test while a blood processing protocol concurrently utilizing said reservoir is being executed by said apparatus.

10. The apparatus of claim 9 wherein said first pump is operated at a predetermined rate different than a rate required by said blood processing protocol to add an additional amount of fluid to said reservoir.

11. The apparatus of claim 10 wherein said second pump is operated at a predetermined rate different than a rate required by said blood processing protocol to remove said additional amount of fluid from said reservoir.

12. The apparatus of claim 11 wherein said control program performs said test for all pumps in said apparatus.

13. The apparatus of claim 12 wherein said control program performs said test for an initial pump compared to each of the remaining pumps in said apparatus.

14. An apparatus for processing blood comprising
   a blood processing path for conducting blood through said apparatus;
   a plurality of pumps for controlling the flow of blood through said path;
   at least one control circuit electrically coupled to said pumps and controlling the operation of said pumps;
   a reservoir in said path, said reservoir configured to contain a fluid, wherein a fluid level of said fluid in said reservoir is variable;
   vent means in fluid communication with said reservoir, said vent means allowing air to pass into and out of said reservoir;
   a first sensor coupled to said reservoir for detecting said fluid level within said reservoir and electrically connected to said control;
   means for performing a test of pump ratios between at least two of said pumps by causing a first pump to pump fluid in a first direction into said reservoir and a second pump to pump fluid in a second direction out of said reservoir and finding a ratio of the action of said first pump to said second pump.

15. The apparatus of claim 14 wherein said means for performing a test of pump ratios further comprises means for beginning said test by raising said fluid level in said reservoir above said first sensor and thereafter lowering said fluid level to said first sensor.

16. The apparatus of claim 15 wherein said means for performing a test of pump ratios further comprises means for causing said first pump to raise said fluid level in said reservoir by operating for a pre-determined number of cycles.

17. The apparatus of claim 16 wherein said means for performing a test of pump ratios further comprises means for causing said second pump to lower said fluid level in said reservoir to said sensor to determine the number of cycles of said second pump need to remove the volume of fluid supplied to the reservoir by said first pump.

18. The apparatus of claim 17 wherein said means for performing a test of pump ratios further comprises means for performing said test for all pumps in said apparatus.

19. The apparatus of claim 18 wherein said means for performing a test of pump ratios further comprises means for performing said test for an initial pump compared to each of the remaining pumps in said apparatus.

20. The apparatus of claim 14 wherein said means for performing a test of pump ratios further comprises means for performing said test for all pumps in said apparatus.

21. The apparatus of claim 20 wherein said means for performing a test of pump ratios further comprises means for performing said test for an initial pump compared to each of the remaining pumps in said apparatus.

22. The apparatus of claim 14 wherein said means for performing a test of pump ratios further comprises means for performing said test while a blood processing protocol concurrently utilizing said reservoir is being executed by said apparatus.

23. The apparatus of claim 22 wherein means for performing a test of pump ratios further comprises means for operating said first pump at a predetermined rate different than a rate required by said blood processing protocol to add an additional amount of fluid to said reservoir.

24. The apparatus of claim 23 wherein means for performing a test of pump ratios further comprises means for operating said second pump at a predetermined rate different than a rate required by said blood processing protocol to remove said additional amount of fluid from said reservoir.

25. The apparatus of claim 24 wherein said means for performing a test of pump ratios further comprises means for performing said test for all pumps in said apparatus.

26. The apparatus of claim 25 wherein said means for performing a test of pump ratios further comprises means for performing said test for an initial pump compared to each of the remaining pumps in said apparatus.

* * * * *